United States Patent

Whittaker et al.

[11] Patent Number: 5,428,168
[45] Date of Patent: Jun. 27, 1995

[54] LACTOL PAF ANTAGONISTS

[75] Inventors: Mark Whittaker, Old Marston; Alan H. Davidson; Zoe M. Spavold, both of Witney; Stephen A. Bowles, Tring, all of United Kingdom

[73] Assignee: British Biotech Pharmaceuticals Limited, Oxford, England

[21] Appl. No.: 940,959
[22] PCT Filed: Apr. 16, 1991
[86] PCT No.: PCT/GB91/00596
 § 371 Date: Oct. 23, 1992
 § 102(e) Date: Oct. 23, 1992
[87] PCT Pub. No.: WO91/17157
 PCT Pub. Date: Nov. 14, 1991

[30] Foreign Application Priority Data

Apr. 27, 1990 [GB] United Kingdom ............... 9009469

[51] Int. Cl.⁶ ............... C07D 471/04; C07D 405/12; C07D 403/12
[52] U.S. Cl. ............... 546/118; 544/335; 546/280; 548/267.8; 548/151
[58] Field of Search ............... 546/283, 118

[56] References Cited

U.S. PATENT DOCUMENTS 4,888,337 12/1989 Godfroid et al. ............... 514/326

FOREIGN PATENT DOCUMENTS

0144804A2 6/1985 European Pat. Off. ........... 546/283
0199324A2 10/1986 European Pat. Off. ........... 549/502
0238202A2 9/1987 European Pat. Off. ........... 514/92

OTHER PUBLICATIONS

Chemical Abstracts, vol. 117, No. 3, Abst. No. 26321Q, Jul. 20, 1992.

Primary Examiner—Alan L. Rotman
Attorney, Agent, or Firm—Allegretti & Witcoff, Ltd.

[57] ABSTRACT

The invention encompasses compounds of general formula I:

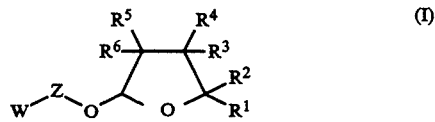

wherein W represents an imidazo[4,5-c]pyridyl group, optionally substituted with one or more substituents selected from $C_1$–$C_6$ alkyl, $C_1$–$C_6$ alkoxy, halo, CF, and CN; and Z, $R^1$, $R^2$, $R^3$, $R^4$, $R^5$, $R^6$ are variables. These compounds are useful as antagonists of platelet activating factor.

12 Claims, No Drawings

LACTOL PAF ANTAGONISTS

This invention relates primarily to novel compounds which are antagonists of platelet activating factor.

Platelet Activating Factor (PAF) is a bioactive phospholipid which has been identified as 1-O-hexadecyl-/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such conditions including asthma, endotoxin shock, glomerulonephritis, immune regulation, transplant rejection, gastric ulceration, psoriasis, embryo implantation and cerebral, myocardial and renal ischemia.

Compounds which have been disclosed as possessing activity as PAF antagonists include compounds which are structurally related to the PAF molecule such as glycerol derivatives (EP-A-0238202), and heterocyclic compounds such as 5-oxy derivatives of tetrahydrofuran (U.S. Pat. No. 4,888,337) and 2,5-diaryl tetrahydrofurans (EP-A-0144804). Recently a more potent 2,5-diaryl tetrahydrofuran derivative, (trans)-2-(3-methoxy-5-methylsulphonyl-4-propoxyphenyl)-5-(3,4,5-trimethoxyphenyl)tetrahydrofuran (L-659,989) has been disclosed (EP-A-0199324).

The compounds of the present invention differ from those such as L-659,989, in that they are substituted butyrolactol ether derivatives rather than 2,5-diaryl tetrahydrofurans. The compounds of the present invention also differ from the 5-oxy derivatives of tetrahydrofuran described in U.S. Pat. No. 4,888,337 in that they do not contain a quaternised nitrogen heterocycle. The present invention provides novel and useful substituted butyrolactol ether derivatives and their pharmaceutically acceptable acid addition salts, and pharmaceutical uses thereof as PAF antagonists.

According to a first aspect of the invention there is provided a compound of general formula I;

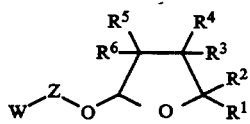

wherein:
W represents a 5- or 6-membered aromatic heterocyclic ring containing one or more non-quaternised sp2 hybridized nitrogen atoms in its ring, which heterocyclic ring may be optionally fused to a benzene ring or to a further 5- or 6-membered aromatic heterocyclic ring containing one or more nitrogen atoms, wherein at least one of the said heterocyclic rings may also contain an oxygen or sulphur atom, and wherein any of the rings may be optionally substituted with one or more substituents selected from $C_1$–$C_6$ alkyl, $C_1$–$C_6$ alkoxy, halo, $CF_3$ and CN;

Z represents
a) a divalent alkanediyl, alkenediyl or alkynediyl group from 2 to 8 carbon atoms which may be a straight or branched-chain having at least 3 carbon atoms in the chain linking W to the oxygen atom, wherein the said group is either unsubstituted or substituted by one or more substituents selected from hydroxy, $C_1$–$C_6$ alkoxy, $C_1$–$C_6$ alkylthio and halo; or
b) a

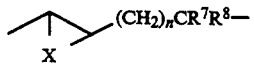

group wherein n is an integer from 0–3, X is O, S or $CH_2$ and each of $R^7$ and $R^8$ is independently hydrogen or $C_1$–$C_6$ alkyl; or
c) a —$(CH_2)_q U(CH_2)_r$— group wherein q is an integer from 0–2, r is an integer from 1–3 and U is a phenylene, furandiyl, tetrahydrofurandiyl, thiophenediyl, tetrahydrothiophenediyl, thiazolediyl or tetrahydrothiazolediyl group;

$R^1$ represents a V group wherein V is a

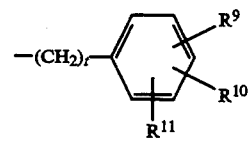

group wherein t is an integer from 0–3 and each of $R^9$, $R^{10}$ and $R^{11}$ is independently hydrogen, $C_1$–$C_6$ alkyl, $C_1$–$C_6$ alkoxy, $C_1$–$C_6$ alkylthio, halo, CN, $NO_2$, $SOC_1$–$C_6$ alkyl, $SO_2C_1$–$C_6$ alkyl, $SO_2(CH_2)_{1-4}CH_2OH$, $SO_2NH_2$, $CO_2H$, $CO_2C_1$–$C_6$ alkyl, CHO, $COC_1$–$C_6$ alkyl, $CH_2OH$, OH, benzyl, benzoyl, $CF_3$, $CONH_2$, $NHCOC_1$–$C_6$ alkyl, or an $NR^{15}R^{16}$ group wherein each of $R^{15}$ and $R^{16}$ is independently hydrogen or $C_1$–$C_6$ alkyl; and
each of $R^2$, $R^3$, $R^4$, $R^5$, and $R^6$ represents independently hydrogen, $C_1$–$C_6$ alkyl, $C_2$–$C_6$ alkenyl, halo, $C_1$–$C_6$ alkoxy, $C_1$–$C_6$ alkylthio, $C_3$–$C_8$ cycloalkyl, $C_4$–$C_8$ cycloalkenyl, $CF_3$, OH, OC(=O)$C_1$–$C_6$ alkyl, a V group, an OV group or an OC(=O)V group;
or a pharmaceutically or veterinarily acceptable acid addition salt or hydrate thereof.

Hereafter in this specification the term "compound" includes "salt" or "hydrate" unless the context requires otherwise.

As used herein the term "halo" means fluoro, chloro, bromo or iodo.

As used herein the term "$C_1$–$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "$C_2$–$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_1$–$C_6$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "$C_1$–$C_6$ alkylthio" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "$C_3$–$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "$C_4$–$C_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination:

W represents a pyridyl (for example 3-pyridyl) group, a pyrimidyl (for example 3-pyrimidyl) group, a triazolyl (for example 1,2,4-triazol-4-yl) group, a benzimidazolyl (for example 2-methylbenzimidazol-1-yl) group or preferably an imidazo [4,5-c]pyrid-1-yl (for example 2-methylimidazo[4,5-c]pyrid-1-yl) group;

Z represents an alkanediyl (for example propylene, 2-hydroxypropylene, 1-methylpropylene, butylene, pentylene and hexylene) group, an alkenediyl (for example prop-2-enylene and hex-5-enylene) group or an alkynediyl (for example prop-2-ynylene, 1-methylprop-2-ynylene, but-3-ynylene, pent-4-ynylene and hex-5-ynylene) group;

U represents a phenylene (for example 1,4-phenylene) group, or a thiazolediyl (for example 2,4-thiazolediyl) group;

q represents an integer of 0 or 1;
r represents an integer of 1 or 2;
t represents an integer of 0;
$R^2$ represents a hydrogen atom;
$R^3$ represents a hydrogen atom;
$R^4$ represents a hydrogen atom;
$R^5$ represents a hydrogen atom or a $C_1$–$C_6$ alkyl (for example methyl) group;
$R^6$ represents a hydrogen atom;
$R^7$ represents a hydrogen atom;
$R^8$ represents a hydrogen atom;
$R^9$ represents a hydrogen atom, a $C_1$–$C_6$ alkoxy (for example methoxy) group or a halogen (for example chlorine) atom;
$R^{10}$ represents a hydrogen atom, a $C_1$–$C_6$ alkoxy (for example methoxy) group or a halogen (for example fluorine, chlorine and bromine) atom;
$R^{11}$ represents a hydrogen atom or a $C_1$–$C_6$ alkoxy (for example methoxy) group;

Particularly preferred compounds include:
1. O-(3-(3-Pyridyl)propyl)-5-(3,4-dimethoxyphenyl)-gamma-butyrolactol ether.
2. O-(4-(3-Pyridyl)but-3-ynyl)-5-(3,4-dimethoxyphenyl)-gamma-butyrolactol ether,
3. O-(4-(3-Pyridyl)butyl)-5-(3,4-dimethoxyphenyl)-gamma-butyrolactol ether,
4. O-(5-(3-Pyridyl)pent-4-ynyl)-5-(3,4-dimethoxyphenyl)-gamma-butyrolactol ether,
5. O-(5-(3-Pyridyl)pentyl)-5-(3,4-dimethoxyphenyl)-gamma-butyrolactol ether,
6. O-(6-(3-Pyridyl)hex-5-ynyl)-5-(3,4-dimethoxyphenyl)-gamma-butyrolactol ether,
7. Z-O-(6-(3-Pyridyl)hex-5-enyl)-5-(3,4-dimethoxyphenyl)-gamma-butyrolactol ether,
8. O-(6-(3-Pyridyl)hexyl)-5-(3,4-dimethoxyphenyl)-gamma-butyrolactol ether,
9. O-(3-(3-Pyridyl)prop-2-ynyl)-5-(3,4-dimethoxyphenyl)-gamma-butyrolactol ether,
10. E-O-(3-(3-Pyridyl)prop-2-enyl)-5-(3,4-dimethoxyphenyl)-gamma-butyrolactol ether,
11. O-(1-Methyl-3-(3-pyridyl)prop-2-ynyl)-5-(3,4-dimethoxyphenyl)-gamma-butyrolactol ether,
12. O-(1-Methyl-3-(3-Pyridyl)propyl)-5-(3,4-dimethoxyphenyl)-gamma-butyrolactol ether,
13. O-(3-(3-Pyridyl)propyl)-5-(4-methoxyphenyl)-gamma-butyrolactol ether,
14. O-(3-(3-Pyridyl)propyl)-5-(3,4,5-trimethoxyphenyl)-gamma-butyrolactol ether,
15. O-(3-(3-Pyridyl)propyl)-5-(4-fluorophenyl)-gamma-butyrolactol ether,
16. O-(3-(3-Pyridyl)propyl)-5-(4-chlorophenyl)-gamma-butyrolactol ether,
17. O-(3-(3-Pyridyl)propyl)-5-(4-bromophenyl)-gamma-butyrolactol ether,
18. O-(3-(3-Pyridyl)propyl)-5-(3,4-dichlorophenyl)-gamma-butyrolactol ether,
19. O-(3-(3-Pyridyl)propyl)-5-(3-chloro-4-methoxyphenyl)-gamma-butyrolactol ether,
20. O-(3-(3-Pyridyl)propyl)-5-phenyl-gamma-butyrolactol ether,
21. O-(2-Hydroxy-3-(3-pyridyl)propyl)-5-(3,4-dichlorophenyl)-gamma-butyrolactol ether,
22. O-(3-(3-Pyridyl)propyl)-3-methyl-5-(3,4-dimethoxyphenyl-gamma-butyrolactol ether,
23. O-((4-(1H-2-Methylbenzimidazyl)phenyl)methyl)5-(3,4-dimethoxyphenyl)-gamma-butyrolactol ether,
24. O-((4-(1H-2-Methybenzimisdiazylmethyl)phenyl)-methyl)-5-(3,4-dimethoxyphenyl)-gamma-butyrolactol ether,
25. O-3-((4-(1H-2-Methylbenzimidazyl)phenyl)propyl) 5-(3,4-dimethoxyphenyl)-gamma-butyrolactol ether,
26. O-((4-(3-Thiazolo[3,2-a]benzimidazyl)phenyl)methyl)-5-(3,4-dimethoxyphenyl)-gamma-butyrolactol ether,
27. O-((2-(3-Pyridyl)-4-thiazolyl)methyl)-5-(3,4-dimethoxyphenyl)-gamma-butyrolactol ether,
28. O-(3-(5-Pyrimidyl)but-3-ynyl)-5-(3,4-dimethoxyphenyl)-gamma-butyrolactol ether,
29. O-(3-(3,5-Dimethyl-1,2,4-triazol-4-yl)propyl)-5-(3,4-dimethoxyphenyl)-gamma-butyrolactol ether;

Most preferred compounds include:
30. O-(3-(1H-2-Methylimidazo[4,5-c]pyridyl)-propyl)-5-(3,4-dimethoxyphenyl)-gamma-butyrolactol ether,
31. O-(4-(1H-2-Methylimidazo[4,5-c]pyridyl)butyl)-5-(3,4-dimethoxyphenyl)-gamma-butyrolactol ether,
32. O-(3-(1H-2-Methylimidazo[4,5-c]pyridyl)propyl)-5-phenyl-gamma-butyrolactol ether, 33. O-(3-(1H-2-Methylimidazo[4,5-c]pyridyl)propyl)-5-(4-fluorophenyl)-gamma-butyrolactol ether,
34. O-(3-(1H-2-Methylimidazo[4,5-c]pyridyl)propyl)-5-(4-bromophenyl)-gamma-butyrolactol ether,
35. O-(3-(1H-2-Methylimidazo[4,5-c]pyridyl)propyl)-5-(3,4-dichlorophenyl)-gamma-butyrolactol ether,
36. O-(3-(1H-2-Methylimidazo[4,5-c]pyridyl)propyl)-5-(3-chloro-4-methoxyphenyl)-gamma-butyrolactol ether,
37. O-(3-(1H-2-Methylimidazo[4,5-c]pyridyl)propyl)-5-(3,4,5-trimethoxyphenyl)-gamma-butyrolactol ether.

Compounds of general formula I may be prepared by any suitable method known in the art and/or by the following process, which itself forms part of the invention.

According to a second aspect of the invention, there is provided a process for preparing a compound of general formula I as defined above, the process comprising:

a) treating a lactol derivative represented by the general formula II

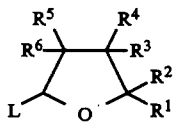

wherein $R^1$, $R^2$, $R^3$, $R^4$, $R^5$, and $R^6$ are as defined in general formula I and L is fluoro, chloro, bromo, iodo, hydroxy, $C_1-C_6$ alkoxy, benzoxy, acetoxy, $OC(NH)CCl_3$, $SO_2Ph$, $C_1-C_6$ alkylthio or SPh with an alcohol of the general formula III

W—Z—OH        III wherein W and Z are as defined in general formula I;

b) treating a lactol represented by the general formula II, wherein $R^1$, $R^2$, $R^3$, $R^4$, $R^5$ and $R^6$ are as defined in general formula I and L is hydroxy with a halide of general formula IV

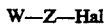
W—Z—Hal        IV wherein W and Z are as defined in general formula I and Hal is fluoro, chloro, bromo or iodo;

c) reducing an unsaturated lactol ether of general formula V

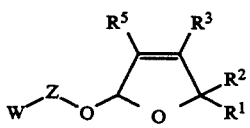

wherein W, Z, $R^1$, $R^2$, $R^3$ and $R^5$ are as defined in general formula I;

d) treating a sulphonyl cyclic ether of general formula VI

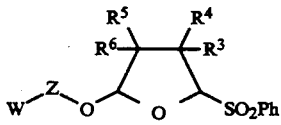

wherein W, Z, $R^3$, $R^4$, $R^5$ and $R^6$ are as defined in general formula I, with a Grignard reagent of general formula VII

$R^1MgBr$        VII wherein $R^1$ is as defined in general formula I except that t is an integer of 0; or e) treating a silyl epoxide of general formula VIII

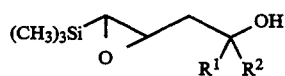

wherein $R^1$ and $R^2$ are as defined in general formula I with an alcohol of general formula III.

The preferred reaction conditions for step (a) vary with the nature of the L group. When the L group is fluoro, chloro, bromo or iodo the reaction may be conducted with an appropriate silver salt (e.g. silver oxide or silver carbonate) and a drying agent (e.g. anhydrous calcium sulphate) either in neat alcohol of general formula III or with one or more equivalents of alcohol of general formula III in an appropriate anhydrous solvent (e.g. acetone). Alternatively, the reaction may be conducted in the presence of a base (e.g. potassium hydroxide) in an appropriate solvent (e.g. acetone). When the L group is hydroxy, $C_1-C_6$ alkoxy, benzoxy, acetoxy, $OC(NH)CCl_3$, the reaction may be conducted with an appropriate Bronsted or Lewis acid catalyst (e.g. p-toluene sulphonic acid, DOWEX 50(H+), boron trifluoride etherate, zinc chloride) either in neat alcohol of general formula III or with one or more equivalents of alcohol of general formula III in an appropriate anhydrous solvent (e.g. dichloromethane). (The word DOWEX is a trademark). When the L group is $SO_2Ph$ the reaction may be conducted with two equivalents of magnesium bromide etherate and one equivalent of solid sodium bicarbonate in tetrahydrofuran. When the L group is SPh the reaction may be conducted with a suitable activating agent (e.g. bromine, N-bromosuccinimide, N-iodosuccinimide, dimethyl(methylthio)sulphonium trifluoromethane sulphonate). The above reactions can be effected at mild temperatures, typically between 0° C. and 50° C.

The reaction of step (b) can for preference be conducted with a silver salt (e.g. silver oxide) in an aprotic solvent (e.g. acetone).

The reaction of step (c) can for preference be conducted with hydrogen in the presence of a suitable catalyst (eg 10% palladium in charcoal).

The reaction of step (d) can for preference be conducted in the presence of anhydrous zinc bromide in dry tetrahydrofuran.

The reaction of step (e) can for preference be conducted with boron trifluoride etherate in a suitable aprotic solvent (e.g. dichloromethane).

The products of general formula I, obtained from step (a), (b), (c), (d) or (e) will be mixtures of one or more pairs of diastereoisomers. These may be separated by physical methods (e.g. flash chromatography).

Lactol derivatives of general formula II may be prepared by a number of methods. The first method for the preparation of lactol derivatives of general formula II, wherein L is hydroxy, involves treatment of an acetal of general formula IX

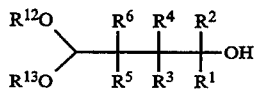

wherein $R^1$, $R^2$, $R^3$, $R^4$, $R^5$ and $R^6$ are as defined in general formula I and each of $R^{12}$ and $R^{13}$ represents a $C_1$–$C_6$ alkyl group or $R^{12}$ and $R^{13}$ together with the oxygen atoms to which they are attached form a 5- or 6-membered ring, with aqueous mineral acid (e.g. 20% sulphuric acid).

Acetals of general formula IX may be prepared by the reaction of a carbonyl compound of general formula X $$R^1\text{—CO—}R^2 \qquad \qquad X$$

wherein $R^1$, and $R^2$ are as defined for general formula IX in general formula I, with a Grignard reagent of general formula XI

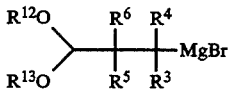

wherein $R^3$, $R^4$, $R^5$ and $R^6$ are as defined in general formula I and $R^{12}$ and $R^{13}$ are defined for general formula IX, in an etheral solvent (e.g. tetrahydrofuran) at 25° C. Carbonyl compounds of general formula X are available in the art or may be prepared by methods analogous to those known in the art. Grignard reagents of general formula XI can be prepared by methods known to those skilled in the art, from material known in the art.

In a second method lactol derivatives of general formula II, wherein L is hydroxy, may be prepared by the reduction of a lactone of general formula XII

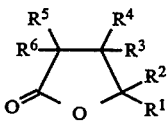

wherein $R^1$, $R^2$, $R^3$, $R^4$, $R^5$ and $R^6$ are as defined in general formula I, with a suitable reducing agent (e.g. diisobutylaluminium hydride) in an appropriate solvent (e.g. toluene).

Lactones of general formula XII are available in the art or may be prepared by methods, known to those skilled in the art, which include the following procedures. The first method involves cyclisation of hydroxy ester of general formula XIII

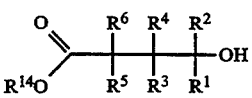

wherein $R^1$, $R^2$, $R^3$, $R^4$, $R^5$ and $R^6$ are as defined in general formula I and $R^{14}$ is $C_1$–$C_6$ alkyl, catalysed by a suitable acid (e.g. p-toluenesulphonic acid).

Hydroxy esters of general formula XIII, wherein $R^2$ is a hydrogen atom, may be prepared by the reduction of keto esters of general formula XIV

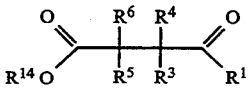

wherein $R^1$, $R^3$, $R^4$, $R^5$ and $R^6$ are as defined in general formula I and $R^{14}$ is as defined above, with a suitable reducing agent (e.g. sodium borohydride). Under certain conditions (sodium cyanoborohydride and hydrochloric acid in tetrahydrofuran at reflux) keto esters of general formula XIV may be converted directly to lactones of general formula XII. Optically active enantiomers of hydroxy esters of general formula XIII may be obtained by utilising a chiral reducing agent (e.g. Bakers' yeast) for the reduction of keto esters of general formula XIV. Keto esters of general formula XIV are available in the art or may be prepared by methods analogous to those known in the art.

In a second method lactones of general formula XIII may be prepared by the treatment of an unsaturated ester of general formula XV

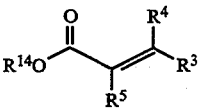

wherein $R^3$, $R^4$, and $R^5$ are as defined in general formula I and $R^{14}$ is as defined above, with a carbonyl compound of general formula X wherein $R^1$, and $R^2$ are as defined in general formula I, with samarium iodide in tetrahydrofuran. Unsaturated esters of general formula XV are available in the art or may be prepared by methods analogous to those known in the art.

Optionally after either of the above methods, a lactone of general formula XII may be converted into another lactone of general formula XII, in one or a plurality of the following methods:

i) by treatment of a lactone of general formula XII, wherein $R^1$, $R^2$, $R^3$, $R^4$, and $R^5$ are as defined in general formula I and $R^6$ is a hydrogen atom with a strong organic non nucleophilic base (e.g. lithium diisopropyl amide) followed by a compound of general formula XVI $$R^6A \qquad \qquad XVI$$

wherein $R^6$ represents a $C_1$–$C_6$ alkyl, $C_3$–$C_8$ cycloalkyl or a V group wherein t is an integer of 1–3 and A is chloro, bromo, iodo, methanesulphonyloxy, p-toluenesulphonyloxy or trifluoromethanesulphonyloxy; and/or ii) by treatment of a lactone of general formula XII, wherein $R^1$, $R^2$, $R^3$ and $R^5$ are as defined in general formula I and each of $R^4$ and $R^6$ is a hydrogen atom with a strong organic non-nucleophilic base (e.g. lithium diisopropyl amide) followed by a compound of general formula XVII $$\text{PhSeCl} \qquad \qquad XVII$$

subsequent treatment with hydrogen peroxide to yield an unsaturated lactone to which is added an appropriate organometallic reagent for example of general formula XVIII $$(R^4)_2\text{CuLi} \qquad \qquad XVIII$$

wherein $R^4$ is as defined in general formula I.

In a third method lactol derivatives of general formula II, wherein L is $C_1$-$C_6$ alkoxy, may be prepared by the treatment of a sulphone of general formula XIX

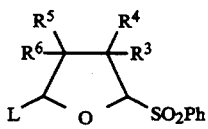   XIX wherein $R^3$, $R^4$, $R^5$, and $R^6$ are as defined in general formula I and L is $C_1$-$C_6$ alkoxy, with a Grignard reagent of general formula XX

   XX wherein $R^1$ is as defined in general formula I except that t is an integer of 0, in the presence of anhydrous zinc bromide in dry tetrahydrofuran.

Sulphones of general formula XIX may be prepared by the reaction of a cyclic ether of general formula XXI

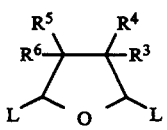   XXI wherein $R^3$, $R^4$, $R^5$, and $R^6$ are as defined in general formula I and L is $C_1$-$C_6$ alkoxy, with one equivalent of benzenesulphinic acid and powdered calcium chloride in dichloromethane. Cyclic ethers of general formula XXI are available in the art or may be prepared by methods analogous to those known in the art.

Optionally, after the above methods, a lactol of general formula II may be converted into another lactol of general formula II, in one or a plurality of the following methods:

i) by treatment of a lactol derivative of general formula II, wherein $R^1$, $R^2$, $R^3$, $R^4$, $R^5$ and $R^6$ are as defined in formula I and L is $C_1$-$C_6$ alkoxy, with benzenesulphinic acid and powdered anhydrous calcium chloride in dichloromethane to give a lactol derivative of general formula II wherein $R^1$, $R^2$, $R^3$, $R^4$, $R^5$ and $R^6$ are as defined in formula I and L is $SO_2Ph$;

ii) by treatment of a lactol derivative of general formula II, wherein $R^1$, $R^2$, $R^3$, $R^4$, $R^5$ and $R^6$ are as defined in formula I and L is hydroxy, with $NCCCl_3$ and sodium hydride in dichloromethane at room temperature to give a lactol derivative of general formula II wherein $R^1$, $R^2$, $R^3$, $R^4$, $R^5$ and $R^6$ are as defined in formula I and L is $OC(NH)CCl_3$;

iii) by treatment of a lactol derivative of general formula II, wherein $R^1$, $R^2$, $R^3$, $R^4$, $R^5$ and $R^6$ are as defined in formula I and L is $C_1$-$C_6$ alkoxy, with $PhSSiMe_3$ in the presence of either trimethylsilyltriflate in dichloromethane or anhydrous zinc iodide and tetrabutylammonium iodide in 1,2-dichloroethane to give a lactol derivative of general formula II wherein $R^1$, $R^2$, $R^3$, $R^4$, $R^5$ and $R^6$ are as defined in formula I and L is SPh;

iv) by treatment of a lactol derivative of general formula II, wherein $R^1$, $R^2$, $R^3$, $R^4$, $R^5$ and $R^6$ are as defined in formula I and L is hydroxy or acetoxy, with a hydrogen halide in acetic anhydride to give a lactol derivative of general formula II wherein $R^1$, $R^2$, $R^3$, $R^4$, $R^5$ and $R^6$ are as defined in formula I and L is fluoro, chloro, bromo or iodo; and/or v) by treatment of a lactol derivative of general formula II, wherein $R^1$, $R^2$, $R^3$, $R^4$, $R^5$ and $R^6$ are as defined in formula I and L is hydroxy, with acetic anhydride and anhydrous zinc halide to give a lactol derivative of general formula II wherein $R^1$, $R^2$, $R^3$, $R^4$, $R^5$ and $R^6$ are as defined in formula I and L is chloro, bromo or iodo.

Alcohols of general formula III are either known compounds or can be prepared conventionally (e.g. by the methods described for the preparation of the Examples).

Halides of general formula IV are available in the art or can be prepared by methods known to those skilled in the art.

Unsaturated lactol ethers of general formula V may be prepared by the treatment of a selenyl substituted lactol ether of general formula XXII

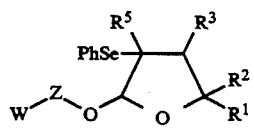   XXII wherein W, Z, $R^1$, $R^2$, $R^3$ and $R^5$, are as defined in general formula I, with hydrogen peroxide.

Selenyl substituted lactol ethers of general formula XXII may be prepared by the reaction of an unsaturated cyclic ether of general formula XXIII

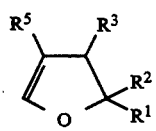   XXIII wherein $R^1$, $R^2$, $R^3$, and $R^5$ are as defined in general formula I, with phenylselenyl bromide and an alcohol of general formula III. Unsaturated cyclic ethers may be prepared by procedures known to those who are skilled in the art.

Sulphonyl cyclic ethers of general formula VI may be prepared by the treatment of a bis-sulphone of general formula XXIV

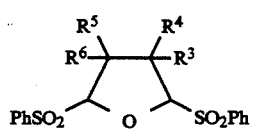   XXIV wherein $R^3$, $R^4$, $R^5$, and $R^6$ are as defined in general formula I, with an alcohol of general formula III in the presence of two equivalents of magnesium bromide etherate and one equivalent of solid sodium bicarbonate in tetrahydrofuran.

Bis-sulphones of general formula XXIV may be prepared by treating a cyclic ether of general formula XXI with benzenesulphinic acid and calcium chloride in dichloromethane.

Silyl epoxides of general formula VIII may be prepared by the reaction of a vinyl silane of general formula XXV

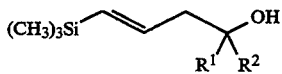

$$XXV$$

wherein R¹ and R² are as defined in general formula I with a peroxy acid (e.g. m-chloroperbenzoic acid) in dichloromethane.

Vinyl silanes of general formula XXV may be prepared by the reaction of a carbonyl compound of general formula X, wherein R¹ and R² are as defined in general formula I, with the allyl anion derived from allyltrimethylsilane and sec-butyllithium in tetrahydrofuran.

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae II, V, VI, and VIII are valuable intermediates in the preparation of compounds of general formula I, as are other novel compounds specifically or generically disclosed herein. According to a third aspect of the invention, there is therefore provided a compound of general formula II. According to a fourth aspect of the invention, there is provided a compound of general formula V. According to a fifth aspect of the invention, there is provided a compound of general formula VI. According to a sixth aspect of the invention, there is provided a compound of general formula VIII.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a seventh aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an eighth aspect of the invention there is provided the use of a compound of general formula I in the preparation of an agent for the treatment of PAF-mediated diseases; and/or the treatment of inflammation such as rheumatoid arthritis, osteoarthritis and eye inflammation, cardiovascular disorder, thrombocytopenia, asthma, endotoxin shock, glomerulonephritis, immune regulation, psoriasis.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a ninth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of "general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or bucal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to the pharmacological example.

The following examples illustrate the invention, but are not intended to limit the scope in any way.

The following abbreviations have been used in the Examples:
DCM—Dichloromethane
DIPE—Diisopropylether
NBS—N-Bromosuccinimide
THF—Tetrahydrofuran

EXAMPLE 1

O-(3-(3-Pyridyl)propyl)-5-(3,4-dimethoxyphenyl)-gamma-butyrolactol ether

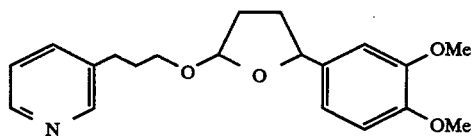

(a) 2-Benzenesulphonyl-5-methoxytetrahydrofuran 2,5-Dimethoxytetrahydrofuran (17.1 ml, 0.13M) was added dropwise to a stirred solution of benzenesulphinic acid (17.0 g, 0.12M) in dry DCM (100 ml) containing a suspension of powdered calcium chloride (1.0 g) at room temperature under argon. After 4 h, the solution was washed with water (2×50 ml), dried over anhydrous sodium sulphate, filtered and evaporated. The product was crystalised (diethyl ether/hexane) to give 2-benzenesulphonyl-5-methoxytetrahydro-furan as a white crystalline solid (15.9 g, 55%).

mp 68° C.

delta$_H$(250 MHz, CDCl$_3$) 7.94 (2H, m), 7.68 (1H, m), 7.57 (2H, m), 5.22 (0.5H, m), 5.12 (0.5H, m), 4.98 (1H, m), 3.37, 3.30 (3H, 2s), 2.64–2.33 (2H, m), 2.06–1.83 (2H, m).

(b)
2-(3,4-Dimethoxyphenyl)-5-methoxytetrahydrofuran

Magnesium (2.18 g, 0.091M) was placed in a 3-necked flask containing dry THF (10 ml) and 1,2-dibromoethane (0.2 ml). A solution of 4-bromoveratrole (18.0 g, 0.086M) in THF (50 ml) was added dropwise, with warming to initiate reaction. The resulting solution was heated at reflux for 0.75 h then cooled to room temperature and cannulated into a 1M solution of ZnBr$_2$ in THF (50 ml, 0.05M) and stirred for 0.5 h at room temperature. A solution of 2-benzenesulphonyl-5-methoxytetrahydrofuran (10.0 g, 0.041M) in THF (50 ml) was added dropwise to the pale yellow suspension and the mixture allowed to stir at room temperature for 20 h. Reaction was quenched by addition of 1N HCl (50 ml), and extracted with ether (2×100 ml). The organics were combined washed with water (50 ml) dried over anhydrous sodium sulphate, filtered and evaporated. Column chromatography (flash silica gel; 3:2 hexane/ethyl acetate) gave 2-(3,4-dimethoxyphenyl)-5-methoxytetrahydrofuran (8.0 g, 82%) as a yellow oil (rf 0.28).

delta$_H$(250 MHz, CDCl$_3$) 7.96 (1H, m), 7.58 (2H, m), 5.33 (0.5H, dd), 5.13 (0.5H, d), 4.98 (1H, m), 3.96 (3H, s), 3.90 (3H, s, OMe), 3.85 (3H, s), 2.53 (2H, m), 2.34 (2H, m).

(c)
2-Benzenesulphonyl-5-(3,4-dimethoxyphenyl)tetrahydrofuran

To a solution of benzenesulphinic acid (8.68 g, 0.061M) in DCM (120 ml) containing a suspension of powdered calcium chloride (1.0 g) at room temperature was added a solution of 2-(3,4,dimethoxybenzyl)-5-methoxytetrahydrofuran (7.0 g, 0.029M) in DCM (80 ml). The mixture was stirred at room temperature for 4 h, quenched by washing with water (2×50 ml), dried over anhydrous sodium sulphate, filtered and evaporated. Column chromatography (flash silica gel; 3:2 hexane/ethyl acetate) provided the product (Rf 0.3) as a clear oil which was crystalized from ethyl acetate/hexane to give 2-benzenesulphonyl-5-(3,4-dimethoxyphenyl)tetrahydrofuran (3.5 g, 35%).

Off white crystalline solid: m.p. 107°–106° C.
Analysis calculated for C$_{18}$H$_{20}$O$_5$S:
Requires C 62.05; H 5.79; S 9.20.
Found C 62.12; H 5.79; S 9.36.
i.r. (KBr) 2960, 1590, 1510 cm$^{-1}$
delta$_H$ (250 MHz, CDCl$_3$) 7.95 (2H, m), 7.66–7.51 (3H, m), 7.35 (0.5H, d, J 1.9 Hz), 6.96 (0.5H, dd, J 8.2, J 1.9 Hz), 6.82 (2H, t, J 8.2 Hz), 5.31 (0.5H, dd,) 5.14 (0.5H, dd, J 7.7, J 5.3 Hz), 4.97 (1H, m), 3.97 (1.5H, s), 3.91 (1.5H, s) 3.86 (3H, s), 2.80–1.60 (4H, m)

(d)
O-(3-(3-Pyridyl)propyl)-5-(3,4-dimethoxyphenyl)-gamma-butyrolactol ether 3-(3-Pyridyl)-1-propanol (0.39 g, 2.9 mmol) was added to a stirred solution of 2-benzenesulphonyl-5-(3,4-dimethoxyphenyl)tetrahydrofuran (0.50 g, 1.4 mmol), magnesium bromide etherate (0.74 g, 2.9 mmol), and sodium bicarbonate (0.24 g, 2.9 mmol) in anhydrous THF. The mixture was stirred at room temperature overnight. Aqueous ammonium chloride (10 ml) was added followed by water (10 ml) and the product extracted into DCM. The combined organics were dried over anhydrous potassium carbonate, filtered and evaporated to give a yellow oil. Column chromatography (flash silica gel; ethyl acetate) gave O-(3-(3-pyridyl)propyl)-5-(3,4-dimethoxyphenyl)-gamma-butyrolactol ether as two diastereoisomers.

Fraction A (trans diastereoisomer): Pale yellow oil.
delta$_H$(250 MHz, CDCl$_3$) 8.47 (2H, br m), 7.53 (1H, d, J 7.8 Hz), 7.21 (1H, dd, J 7.4, 4.7 Hz), 6.86 (3H, m), 5.32 (1H, dd, J 5.2, 1.9 Hz, CHOO), 5.03 (1H, t, J 7.2 Hz, OCHAr), 3.90 (3H, s), 3.88 (3H, s), 3.81 (1H, dt, J 9.8, 6.4 Hz), 3.46 (1H, dt, J 9.8, 6.4 Hz), 2.73 (2H, t, J 7.7 Hz), 2.43–1.75 (6H, m).

delta$_C$ (62.90 MHz, CDCl$_3$) 149.83, 148.84, 148.21, 147.14, 137.02, 135.66, 134.68, 123.09, 116.09, 110.88, 108.93, 104.16, 79.02, 66.16, 55.73, 55.64, 32.71, 32.38, 30.86, 29.41.

Mass spec. [CI, NH$_3$]: 344 [M+H]$^+$.

Fraction B (cis diastereoisomer): Pale yellow oil.
delta$_H$(250 MHz, CDCl$_3$) 8.40 (2H, br m), 7.50 (1H, d, J 7.8 Hz), 7.13 (1H, dd, J 7.8, J 4.8 Hz), 6.97–6.76 (3H, m), 5.18 (1H, d, J 3.5 Hz, CHOO), 4.97 (1H, t, J 6.6 Hz, OCHAr), 3.88 (3H, s), 3.87 (3H, s), 3.86 (1H, m,), 3.45 (H, dt, J 9.7, 6.4 Hz), 2.72 (2H, t, J 7.7 Hz), 2.30–1.80 (6H, m).

delta$_C$ (62.90 MHz, CDCl$_3$) 149.73, 148.86, 148.30, 147.17, 137.00, 135.68, 135.58, 123.18, 118.62, 110.76, 109.57, 104.10, 82.53, 66.22, 55.79, 55.60, 33.76, 32.67, 30.91, 29.51.

Mass spec. [CI, NH$_3$]: 344 [M+H]+.

EXAMPLE 2

O-(4-(3-Pyridyl)but-3-ynyl)-5-(3,4-dimethoxyphenyl)-gamma-butyrolactol ether

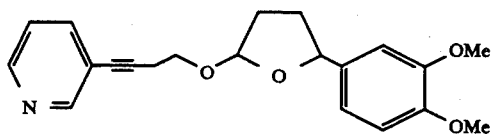

(a) 4-(3-Pyridyl)-1-but-3-ynol

To a stirred solution of 3-bromopyridine (3.75 g, 23.8 mmol), 3-butyn-1-ol (2.0 g, 28.5 mmol) and triethylamine (12 ml) in anhydrous DCM was added bis(triphenylphosphine)palladium dichloride (0.05 g, 0.07 mmol) and copper(I) iodide (0.05 g, 0.26 mmol). The mixture was refluxed for 20 h under argon. After cooling, water (20 ml) was added and the product extracted into DCM. The combined organics were dried over anhydrous potassium carbonate, filtered and evaporated to give a brown oil. Column chromatography (flash silica gel, ethyl acetate) gave 4-(3-pyridyl)-1-but-3-ynol (0.43 g, 12%) as a colourless oil.

delta$_H$(250 MHz, CDCl$_3$) 8.48 (1H, s), 8.32 (1H, d, J 3.8 Hz), 7.55 (1H, dt, J 6.0, 1.9 Hz), 7.07 (1H, dd, J 7.8, 4.9 Hz), 4.79 (1H, br s), 3.73 (2H, t, J 6.6 Hz), 2.58 (2H, t, J 6.6 Hz).

(b) O-(4-(3-Pyridyl)but-3-ynyl)-5-(3,4-dimethoxyphenyl)-gamma-butyrolactol ether O-(4-(3-Pyridyl)but-3-ynyl)-5-(3,4-dimethoxyphenyl)-gamma-butyrolactol ether was prepared by the procedure described in Example 1(d) employing 4-(3-pyridyl)-1-but-3-ynol in lieu of 3-(3-pyridyl)-1-propanol.

55:45 Mixture of trans and cis diastereoisomers: Yellow oil.

delta$_H$(250 MHz, CDCl$_3$) 8.63 (1H, br s), 8.49 (1H, d, J 4.6 Hz), 7.66 (1H, m), 7.20 (1H, dd, J 7.9, 4.9 Hz), 6.87 (3H, m), 5.42 (0.55H, dd, J 5.3, 1.8 Hz), 5.27 (0.45H, d, J 3.8 Hz), 5.02 (1H, m), 3.96 (1H, m), 3.89, 3.87, 3.84 (6H 3s), 3.71 (1H, m), 2.75 (2H, t, J 6.9 Hz), 2.42–1.71 (4H, m)

delta$_C$ (62.90 MHz, CDCl$_3$) 152.27, 148.92, 148.83, 148.37, 148.00, 138.43, 135.41, 135.58, 122.81, 118.71, 118.15, 110.92, 110.86, 109.60, 108.95, 104.28, 104.13, 90.72, 90.47, 82.87, 79.24, 65.40, 65.32, 55.85, 55.78, 55.67, 33.85, 32.59, 32.47, 20.99, 20.89.

EXAMPLE 3

O-(4-(3-Pyridyl)butyl)-5-(3,4-dimethoxyphenyl)-gamma-butyrolactol ether

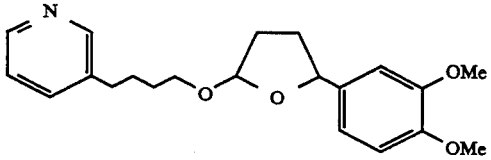

O-(4-(3-Pyridyl)but-3-ynyl)-5-(3,4-dimethoxyphenyl)-gamma-butyrolactol ether (0.10 g, 0.28 mmol) was added to a stirred suspension of 10% palladium on charcoal (0.15 g) in methanol (5 ml). The reaction was stirred at room temperature under hydrogen for 4 h, by which time hydrogen uptake had ceased. The mixture was filtered through celite and evaporated to give a yellow oil. Column chromatography (flash silica gel; 3% methanol in ethyl acetate) gave O-(4-(3-pyridyl)butyl)-5-(3,4-dimethoxyphenyl)-gamma-butyrolactol ether (96 mg, 96%) as a colourless oil (60:40 mixture of trans and cis diastereoisomers).

delta$_H$ (250 MHz CDCl$_3$) 8.45 (2H, br s), 7.50 (1H, m), 7.21 (1H, dd, J 7.8, 4.8 Hz), 6.97–6.76 (3H, m), 5.32 (0.6H, dd, J 5.3, 1.9 Hz, CHOO), 5.17 (0.4H, m, CHOO), 5.05–4.92 (1H, m, OCHAr), 3.90, 3.88, 3.87, 3.84 (6H, 4s), 3.82 (1H, m), 3.47 (1H, m), 2.66 (2H, m), 2.44–1.52 (8H, m).

EXAMPLE 4

O-(5-(3-Pyridyl)pent-4-ynyl)-5-(3,4-dimethoxyphenyl)-gamma-butyrolactol ether

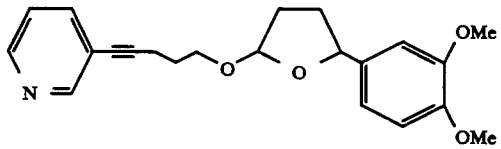

(a) 5-(3-Pyridyl)-1-pent-4-ynol

Utilising the procedure described in Example 2(a) employing 4-pentyn-1-ol in lieu of 3-butyn-1-ol gave 5-(3-pyridyl)-1-pent-4-ynol as a colourless oil.

delta$_H$(250 MHz, CDCl$_3$) 8.61 (1H, d), 8.45 (1H, dd), 7.66 (1H, dt), 7.21 (1H, dd), 3.80 (2H, t), 2.56 (2H, t), 2.39 (1H, br s), 1.87 (2H, m).

(b) O-(5-(3-Pyridyl)pent-4-ynyl)-5-(3,4-dimethoxyphenyl)-gamma-butyrolactol ether O-(5-(3-Pyridyl)pent-4-ynyl)-5-(3,4-dimethoxyphenyl)-gamma-butyrolactol ether was prepared by the procedure described in Example 1(d) employing 5-(3-pyridyl)-1-pent-4-ynol in lieu of 3-(3-pyridyl)-1-propanol.

60:40 Mixture of trans and cis diastereoisomers: Yellow oil.

delta$_H$ (250 MHz CDCl$_3$) 8.59 (1H, t, J 0.8 Hz), 8.44 (1H, m), 7.60 (1H, d, J 7.8 Hz), 7.14 (1H, m), 6.97–6.71 (3H, m), 5.33 (0.6H, dd, J 5.2, 1.8 Hz, CHOO), 5.19 (0.4H, d, J 3.7 Hz, CHOO), 5.05–4.86 (1H, m, OCHAr), 3.91 (1H, m), 3.86, 3.85, 3.83, 3.81 (6H, 4s), 3.56 (1H, m), 2.53 (2H, dt, J 7.0, 1.5 Hz), 2.45–1.66 (6H, m).

delta$_C$ (62.90 MHz, CDCl$_3$) 152.18, 148.89, 148.27, 147.86, 138.34, 135.58, 134.71, 122.77, 120.90, 120.85, 118.65, 118.18, 110.89, 110.78, 109.52, 108.94, 104.20, 93.17, 93.08, 82.67, 79.08, 65.87, 65.70, 55.82, 55.73, 33.82, 32.78, 32.69, 32.47, 28.72, 28.62, 16.31, 16.21.

EXAMPLE 5

O-(5-(3-Pyridyl)pentyl)-5-(3,4-dimethoxyphenyl)-gamma-butyrolactol ether

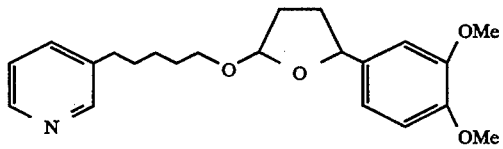

O-(5-(3-Pyridyl)pentyl)-5-(3,4-dimethoxyphenyl)-gamma-butyrolactol ether was prepared by the procedure described in Example 3 employing O-(5-(3-pyridyl)pent-4-ynyl)-5-(3,4-dimethoxyphenyl)-gamma-butyrolactol ether as starting material.

Fraction A (trans diastereoisomer): Yellow oil.

delta$_H$(250 MHz, CDCl$_3$) 8.43, (2H, br s), 7.46 (1H, d, J 7.8 Hz), 7.18 (1H, dd, J 7.4, 4.8 Hz), 6.92–6.76 (3H, m), 5.30 (1H, dd, J 5.3, 1.8 Hz, CHOO), 4.98 (1H, t, J 7.2, OCHAr), 3.88 (3H, s), 3.85 (3H, s), 3.74 (1H, m), 3.42 (1H, m), 2.61 (2H, t, J 7.6 Hz), 2.42–1.31 (10 H, m).

delta$_C$ (62.90 MHz, CDCl$_3$) 149.79, 148.92, 148.29, 147.08, 135.69, 134.80, 123.17, 118.18, 110.89, 108.95, 104.16, 79.02, 67.26, 55.80, 55.75, 32.84, 32.76, 32.45, 30.80, 29.41, 25.67.

Fraction B (cis diastereoisomer): Yellow oil.

delta$_H$ (250 MHz, CDCl$_3$) 8.43 (2H, br s), 7.46 (1H, dt, J 7.8, 1.4 Hz), 7.18 (1H, dd, J 7.7, 4.8 Hz), 6.98–6.78 (3H, m), 5.16 (1H, d, J 3.4 Hz, CHOO), 4.94 (1H, t, J 7.2 Hz, OCHAr), 3.86, (3H, s), 3.85 (3H, s), 3.80 (1H, m), 3.41 (1H, m), 2.60 (2H, t, J 7.6 Hz), 2.40–1.33 (10H, m).

delta$_C$ (62.90 MHz, CDCl$_3$) 149.81, 148.88, 148.28, 147.15, 135.69, 135.62, 123.14, 118.70, 110.69, 109.53, 104.05, 82.57, 67.22, 55.82, 55.62, 33.80, 32.82, 30.86, 29.45, 25.75.

EXAMPLE 6

O-(6-(3-Pyridyl)hex-5-ynyl)-5-(3,4-dimethoxyphenyl)-gamma-butyrolactol ether

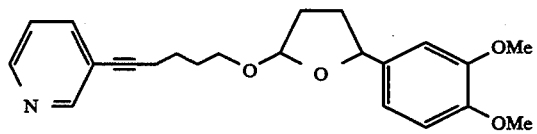

(a) 6-(3-Pyridyl)-1-hex-5-ynol

Utilising the procedure described in Example 2(a) employing 5-hexyn-1-ol in lieu of 3-butyn-1-ol gave 6-(3-pyridyl)-1-hex-5-ynol as a colourless oil.

delta$_H$(250 MHz, CDCl$_3$) 8.62 (1H, br s), 8.49 (1H, br s), 7.66 (1H, m), 7.22 (1H, m), 3.70 (2H, t), 2.47 (2H, t), 2.32 (1H, br s), 1.73 (4H, m).

(b)
O-(6-(3-Pyridyl)hex-5-ynyl)-5-(3,4-dimethoxyphenyl)-gamma-butyrolactol ether O-(6-(3-Pyridyl)hex-5-ynyl)-5-(3,4-dimethoxyphenyl)-gamma-butyrolactol ether was prepared by the procedure described in Example 1(d) employing 6-(3-pyridyl)-1-hex-5-ynol in lieu of 3-(3-pyridyl)-1-propanol.

Fraction A (trans diastereoisomer): Yellow oil.

delta$_H$(250 MHz CDCl$_3$) 8.60 (1H, d, J 1.5 Hz), 8.43 (1H, dd, J 4.9, 1.5 Hz), 7.62 (1H, dt, J 7.9, 1.9 Hz), 7.15 (1H, ddd, J 7.8, 4.9, 0.7 Hz), 6.82 (3H, m), 5.31 (1H, dd, J 5.2, 1.9 Hz, CHOO), 4.99 (1H, t, J 7.2 Hz, OCHAr), 3.85 (3H, s), 3.82 (3H, s), 3.80 (1H, m), 3.77 (1H, m), 2.44 (2H, t, J 6.7 Hz), 2.41–1.60 (8H, m).

delta$_C$ (62.90 MHz, CDCl$_3$) 152.17, 148.89, 148.26, 147.77, 138.31, 134.76, 122.78, 120.97, 118.16, 110.89, 108.95, 104.16, 93.62, 79.04, 77.49, 66.78, 55.72, 32.75, 32.44, 28.87, 25.24, 19.13.

Fraction B (20:80 mixture of trans and cis diastereoisomers): Yellow oil.

delta$_H$(250 MHz, CDCl$_3$) 8.60 (1H, d, J 1.1 Hz), 8.46 (1H, dd, J 4.8, 1.5 Hz), 7.64 (1H, dt, J 7.9, 1.9 Hz), 7.18 (1H, dd, 7.5, 4.9 Hz), 6.97–6.79 (3H, m), 5.33 (0.2H, dd, J 5.2, 1.9 Hz, CHOO), 5.18 (0.8H, d, J 3.5 Hz, CHOO), 4.97 (1H, m, OCHAr), 3.87, 3.86, 3.85, 3.83 (6H, 4s), 3.84 (1H, m), 3.48 (1H, dt, J 9.5, 6.3 Hz), 2.45 (2H, t, J 6.8 Hz), 2.40–1.63 (8H, m).

delta$_C$ (62.90 MHz, CDCl$_3$) 152.18, 148.89, 148.29, 147.86, 147.80, 138.31, 135.65, 122.81, 118.71, 118.18, 110,89, 110.70, 109.51, 108.95, 104.19, 104.09, 93.48, 82.63, 79.05, 66.61, 55.79, 55.73, 55.67, 33.82, 32.85, 32.75, 32.47, 28.90, 25.36, 19.20, 19.17.

EXAMPLE 7

Z-O-(6-(3-Pyridyl)hex-5-enyl)-5-(3,4-dimethoxyphenyl)-gamma-butyrolactol ether

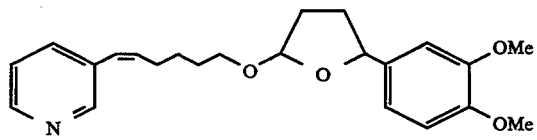

(a) Z-6-(3-Pyridyl)-1-hex-5-enol 6-(3-Pyridyl)-1-hex-5-ynol (0.15 g, 0.86 mmol) was added to a stirred suspension of 10% palladium on charcoal (20 mg) in ethanol. The reaction was stirred at room temperature under hydrogen for 24 h. The mixture was filtered through celite and evaporated to give a clear oil. Column chromatography (flash silica gel; ethyl acetate) gave Z-6-(3-pyridyl)-1-hex-5-enol (70 mg, 46%).

delta$_H$(250 MHz, CDCl$_3$) 8.47 (1H, d), 8.39 (1H, dd), 7.55 (1H, dt), 7.25 (1H, dd), 6.34 (1H, d), 5.79 (1H, dt), 3.58 (2H, t), 3.29 (1H, br s), 2.30 (2H, m), 1.57 (4H, m).

(b) Z-O-(6-(3-Pyridyl)hex-2-enyl)-5-(3,4-dimethoxyphenyl)-gamma-butyrolactol ether Z-O-(6-(3-Pyridyl)hex-2-enyl)-5-(3,4-dimethoxyphenyl)-gamma-butyrolactol ether was prepared by the procedure described in Example 1(d) employing Z-6-(3-pyridyl)-1-hex-5-enol in lieu of 3-(3-pyridyl)-1-propanol.

Fraction A (trans diastereoisomer): Yellow oil.

delta$_H$(250 MHz, CDCl$_3$) 8.53 (1H, br s), 8.45 (1H, br s), 7.56 (1H, dt, J 7.8, 1.7 Hz), 7.24 (1H, dd, J 7.8, 4.8 Hz), 6.86 (3H, m), 6.37 (1H, d, J 11.7 Hz), 5.80 (1H, dt, J 11.6, 7.3 Hz), 5.30 (1H, dd, J 5.2, 2.0 Hz, CHOO), 4.99 (1H, t, J 7.2 Hz, OCHAr), 3.89 (3H, s), 3.86 (3H, s), 3.75

(1H, dt J 9.7, 6.4 Hz), 3.43 (1H, dt, J 9.7, 6.3 Hz), 2.37 (3H, m), 2.21 (1H, m), 1.95 (1H, m), 1.85–1.45 (5H, m).

delta$_C$ (62.90 MHz, CDCl$_3$) 149.60, 149.00, 148.30, 147.42, 135.56, 135.14, 134.84, 125.33, 122.80, 118.18, 110.95, 109.01, 104.16, 79.03, 67.16, 55.86, 55.76, 32.76, 32.45, 29.28, 28.28, 26.40.

Fraction B (35:65 mixture of trans and cis diastereoisomers): Yellow oil.

delta$_H$(250 MHz, CDCl$_3$) 8.53 (1H, br s), 8.44 (1H, br s), 7.55 (1H, d, J 7.8 Hz), 7.24 (1H, dd, J7.7, 4.9 Hz), 6.95–6.75 (3H, m), 6.36 (1H, d, J 11.8 Hz), 5.78 (1H, dt, J 11.6, 7.3 Hz), 5.30 (0.35H, dd, J 5.2, 2.0 Hz, CHOO), 5.15 (0.65H, d, J 3.5 Hz, CHOO), 4.95 (1H, m, OCHAr), 3.89 (3H, s), 3.86 (3H, s), 3.80 (1H, m), 3.41 (1H, m), 2.40–1.45 (10H, m).

delta$_C$ (62.90 MHz, CDCl$_3$) 149.74, 148.92, 148.29, 147.41, 135.71, 135.54, 135.12, 134.96, 134.83, 125.41, 125.32, 122.80, 118.73, 118.18, 110.92, 110.73, 109.55, 109.11, 104.15, 104.06, 82.59, 79.02, 67.13, 55.84, 55.76, 55.66, 33.79, 32.84, 32.75, 32.45, 29.28, 28.31, 26.49, 26.40.

EXAMPLE 8

O-(6-(3-Pyridyl)hexyl)-5-(3,4-dimethoxyphenyl)-gamma-butyrolactol ether

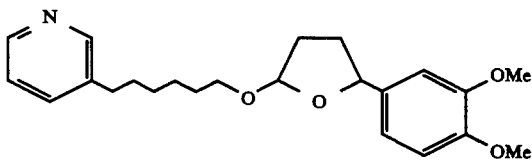

(a) 6-(3-Pyridyl)-1-hexanol 6-(3-Pyridyl)-1-hexanol was prepared following the procedure described in Example 7(a) allowing the reduction to proceed to completion.

delta$_H$ (250 MHz, CDCl$_3$) 8.35 (2H, br s), 7.45 (1H, d), 7.18 (1H, dd), 3.60 (2H, t), 3.40 (1H, br s), 2.55 (2H, t), 1.65–1.20 (8H, m).

(b) O-(6-(3-Pyridyl)hexyl)-5-(3,4-dimethoxyphenyl)-gamma-butyrolactol ether

O-(6-(3-Pyridyl)hexyl)-5-(3,4-dimethoxyphenyl)-gamma-butyrolactol ether was prepared by the procedure described in Example 1(d) employing 6-(3-pyridyl)-1-hexanol in lieu of 3-(3-pyridyl)-1-propanol.

Fraction A (trans diastereoisomer): Yellow oil.

delta$_H$(250 MHz, CDCl$_3$) 8.43 (2H, br s), 7.47 (1H, d, J 7.8 Hz), 7.19 (1H, dd, J 7.7, 4.8 Hz), 6.87 (3H, m), 5.31 (1H, dd, J 5.2, 1.9 Hz, CHOO), 5.00 (1H, t, J 7.2 Hz, OCHAr), 3.89 (3H, s), 3.86 (3H, s), 3.74 (1H, dt, J 9.6, 6.7 Hz), 3.42 (1H, dt, J 9.6, 6.6 Hz), 2.60 (2H, t, J 7.6 Hz), 2.45–2.10 (2H, m), 1.95 (1H, m), 1.80–1.50 (5H, m), 1.40 (4H, m).

delta$_C$ (62.90 MHz, CDCl$_3$) 149.80, 148.95, 148.29, 147.05, 137.75, 135.65, 134.86, 123.14, 118.18, 110.94, 109.01, 104.16, 79.00, 67.41, 55.85, 55.76, 32.84, 32.75, 32.47, 30.94, 29.54, 28.81, 25.90.

Fraction B: (45:55 mixture of trans and cis diastereoisomers): Yellow oil.

delta$_H$(250 MHz, CDCl$_3$) 8.41 (2H, br s), 7.5 (1H, d, J 7.8 Hz), 7.16 (1H, dd, J 7.6, 4.9 Hz), 6.98–6.75 (3H, m), 5.30 (0.45H, dd, J 5.2, 1.9 Hz, CHOO), 5.15 (0.55H, d, J 3.5 Hz, CHOO), 5.05–4.90 (1H, m, OCHAr), 3.87, 3.86, 3.85, 3.83 (6H, 4s), 3.75 (1H, m), 3.42 (1H, m), 2.57 (2H, t, J 7.6 Hz), 2.45–1.20 (12H, m).

delta$_C$ (62.90 MHz, CDCl$_3$) 149.73, 148.87, 148.24, 147.02, 137.61, 135.73, 135.57, 134.81, 123.07, 118.67, 118.13, 110.90, 110.66, 109.51, 108.96, 104.08, 103.99, 82.51, 78.94, 67.32, 55.78, 55.68, 55.58, 33.74, 32.82, 32.74, 32.39, 30.88, 29.50, 28.82, 28.73, 25.96, 25.83.

EXAMPLE 9

O-(3-(3-Pyridyl)prop-2-ynyl)-5-(3,4-dimethoxyphenyl)-gamma-butyrolactol ether

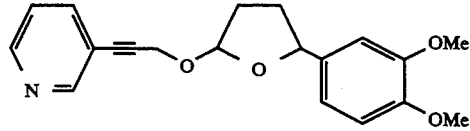

(a) 3-(3-Pyridyl)-1-prop-2-ynol

Utilising the procedure described in Example 2(a) employing 2-propyn-1-ol in lieu of 3-butyn-1-ol gave 3-(3-pyridyl)-1-prop-2-ynol as a colourless oil.

delta$_H$(250 MHz, CDCl$_3$) 8.79 (1H, d), 8.54 (1H, dd), 7.76 (1H, dt), 7.28 (1H, dd), 4.51 (2H, s), 3.67 (1H, br s).

(b) O-(3-(3-Pyridyl)prop-2-ynyl)-5-(3,4-dimethoxyphenyl)-gamma-butyrolactol ether O-(3-(3-Pyridyl)prop-2-ynyl)-5-(3,4-dimethoxyphenyl)-gamma-butyrolactol ether was prepared by the procedure described in Example 1(d) employing 3-(3-pyridyl)-1-prop-2-ynol in lieu of 3-(3-pyridyl)-1-propanol.

Fraction A (trans diastereoisomer): Yellow oil.

delta$_H$(250 MHz, CDCl$_3$) 8.50 (2H, br m) J 7.75 (1H, d, J 7.8 Hz), J 7.26 (1H, br m), 6.88 (2H, s), 6.86 (1H, s), 5.57 (1H, dd, J 5.1, J 1.7 Hz, CHOO), 5.08 (1H, t, J 7.2 Hz, OCHAr), 4.54 (2H, d, J 4.8 Hz), 3.90 (3H, s,), 3.88 (3H, s), 2.43 (1H, m), 2.29 (1H, m), 2.05 (1H, m), 1.82 (1H, m).

Fraction B (20:80 mixture of trans and cis diastereoisomers): Yellow oil.

delta$_H$(250 MHz, CDCl$_3$) 8.67 (1H, d, J 1.8 Hz), 8.55 (1H, dd, J 4.7, J 1.5 Hz), 7.74 (1H, dt, J 7.8, 1.9 Hz), 7.26 (1H, dd, J 7.8, 4.9 Hz), 6.91 (3H, m), 5.58 (0.2H, dd, J 5.2, 1.7 Hz, CHOO), 5.42 (0.8H, d, J 4.0 Hz, CHOO), 5.06 (1H, m, OCHAr), 4.57 (2H, m), 3.92 (3H, s), 3.88 (3H, s), 2.45–1.78 (4H, m)

EXAMPLE 10

E-O-(3-(3-Pyridyl)prop-2-enyl)-5-(3,4-dimethoxyphenyl)-gamma-butyrolactol ether

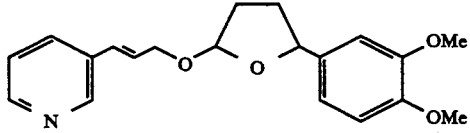

(a) Methyl E-3-(3-pyridyl)acrylate

3-Bromopyridine (4 g, 25 mmol), methyl acrylate (2.6 g, 31 mmol), palladium(II) acetate (0.26 g, 1.2 mmol), tri-o-tolylphosphine (0.74 g, 2.4 mmol) and triethylamine (10 ml) were placed in a thick walled glass tube. The tube was sealed under argon and the mixture heated at 80° C. After 12 h the reaction mixture was allowed to cool to room temperature and chloroform (100 ml) was added. The mixture was washed with water (2×100 ml), the organics dried over anhydrous magnesium sulphate, and the solvent removed under reduced pressure. Column chromatography (flash silica gel; 1:1 ethyl acetate/hexane) yielded methyl E-3-(3-pyridyl)acrylate as a colourless oil (0.5 g, 12%).

delta$_H$(250 MHz, CDCl$_3$) 8.65 (1H, d, J 2.1 Hz), 8.51 (1H, dd, J 4.8, 1.5 Hz), 7.75 (1H, dt, J 8.0, 1.9 Hz), 7.59 (1H, d, J 16.1 Hz), 7.24 (1H, dd, J 7.9, 4.8 Hz), 6.43 (1H, d, J 16.1 Hz), 3.73 (3H, s).

(b) E-3-(3-Pyridyl)-1-prop-2-enol

To an ice cold mixture of lithium aluminium hydride (28 mg, 0.74 mmol) in dry diethyl ether (20 ml) was added dropwise methyl E-3-(3-pyridyl)acrylate (100 mg, 0.61 mmol) under argon. The resulting mixture was allowed to warm up to room temperature and stirred for 12 h. Water (0.1 ml), 15% aqueous sodium hydroxide (0.1 ml) and water (0.3 ml) were added sequentially over 0.5 h and the mixture allowed to stir for 1 h. The resulting suspension was filtered and the filtrate concentrated under reduced pressure. Flash chromatography (flash silica gel; 10% methanol in ethyl acetate) gave 3-(3-pyridyl)-1-propanol, which was discarded, and E-3-(3-pyridyl)-1-prop-2-enol (55 mg, 67%) as a colourless oil.

delta$_H$(250 MHz, CDCl$_3$) 8.63 (1H, br s), 8.50 (1H, br s), 7.75 (1H, d, J 7.9 Hz), 6.63 (1H, d, J 16.1 Hz), 6.52–6.37 (2H, m), 4.37 (2H, dd, J 5.2, 1.4 Hz), 2.27 (1H, br s).

(c) E-O-(3-(3-Pyridyl)prop-2-enyl)-5-(3,4-dimethoxyphenyl)-gamma-butyrolactol ether E-O-(3-(3-Pyridyl)prop-2-enyl)-5-(3,4-dimethoxyphenyl)-gamma-butyrolactol ether was prepared by the procedure descibed in Example 1(d) employing E-3-(3-pyridyl)-1-prop-2-enol as starting material.

Fraction A (trans diastereoisomer): Yellow oil.

delta$_H$(250 MHz, CDCl$_3$) 8.62 (1H, br s), 8.47 (1H, br d, J 3.8 Hz), 7.72 (1H, dt, J 7.9, 1.8 Hz), 7.25 (1H, dd, J 7.9, 4.8 Hz), 6.95–6.80 (3H, m), 6.64 (1H, d, J 16.1 Hz), 6.41 (1H, dt, J 16.1, 5.6 Hz), 5.44 (1H, dd, J 5.2, 1.8 Hz, CHOO), 5.08 (1H, t, J 7.2 Hz, OCHAr), 4.47 (1H, ddd, J 13.3, 5.3, 1.4 Hz), 4.22 (1H, ddd, J 13.2, 6.0, 1.3 Hz), 3.90 (3H, s), 3.88 (3H, s), 2.43 (1H, m), 2.29 (1H, m), 2.07 (1H, m), 1.82 (1H, m).

delta$_C$ (62.90 MHz, CDCl$_3$) 148.98, 148.52, 148.42, 148.26, 134.55, 132.83, 132.40, 128.54, 128.26, 123.20, 118.24, 110.98, 109.04, 103.79, 79.34, 67.50, 55.88, 55.79, 32.67, 32.52.

Fraction B (cis diastereoisomer): Yellow oil.

delta$_H$(250 MHz, CDCl$_3$) 8.60 (1H, br s), 8.48 (1H, br d, J 3.7 Hz), 7.68 (1H, dt, J 7.9, 1.9 Hz), 7.25 (1H, dd, J 7.8, 4.8 Hz), 7.00–6.80 (3H, m), 6.64 (1H, d, J 16.1 Hz), 6.40 (1H, dt, J 16.0, 5.5 Hz), 5.29 (1H, d, J 3.9 Hz, CHOO), 5.08 (1H, dd, J 8.9, 6.4 Hz, OCHAr), 4.50 (1H, ddd, J 13.4, 5.2, 1.5 Hz), 4.23 (1H, ddd, J 13.4, 5.8, 1.4 Hz), 3.87 (3H, s), 3.83 (3H, s), 2.35–1.95 (4H, m).

delta$_C$ (62.90 MHz, CDCl$_3$) 149.00, 148.55, 148.40, 148.17, 135.43, 132.76, 132.40, 128.45, 128.04, 123.40, 118.93, 110.73, 109.63, 103.47, 82.96, 67.22, 55.86, 55.70, 34.00, 32.70.

EXAMPLE 11

O-(1-Methyl-3-(3-pyridyl)prop-2-ynyl)-5-(3,4-dimethoxyphenyl)-gamma-butyrolactol ether

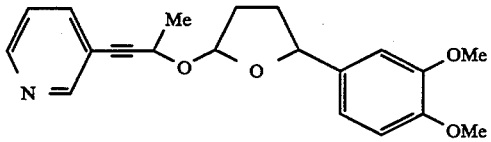

(a) 1-Methyl-3-(3-pyridyl)-1-prop-2-ynol

Utilising the procedure described in Example 2(a) employing 3-butyn-2-ol in lieu of 3-butyn-1-ol gave 1-methyl-3-(3-pyridyl)-1-prop-2-ynol as a colourless oil.

delta$_H$(250 MHz, CDCl$_3$) 8.66 (1H, d, J 1.9 Hz), 8.43 (1H, dd, J 5.0, 1.7 Hz), 7.65 (1H, dt, J 7.9, 1.9 Hz), 7.19 (1H, dd, J 7.9, 4.9 Hz), 4.71 (1H, q, J 6.6 Hz), 4.73 (1H, br s), 1.50 (3H, d, J 6.6 Hz).

(b) O-(1-Methyl-3-(3-pyridyl)prop-2-ynyl)-5-(3,4-dimethoxyphenyl)-gamma-butyrolactol ether O-(1-Methyl-3-(3-Pyridyl)prop-2-ynyl)-5-(3,4-dimethoxyphenyl)-gamma-butyrolactol ether was prepared by the procedure described in Example 1(d) employing 1-methyl-3-(3-pyridyl)-1-prop-2-ynol in lieu of 3-(3-pyridyl)-1-propanol.

20:40:40 Mixture of 3 diastereoisomers: Colourless oil.

delta$_H$(250 MHz, CDCl$_3$) 8.66 (1H, br s), 8.50 (1H, br s), 7.68 (1H, m), 7.20 (1H, m), 6.95–6.76 (3H, m), 5.75 (0.2H, m, CHOO), 5.61 (0.4H, d, J 3.0 Hz, CHOO), 5.40 (0.4H, dd, J 5.1, 1.5 Hz, CHOO), 5.16 (0.4H, t, J 7.2 Hz, OCHAr), 5.00 (0.6H, m, OCHAr), 4.82 (0.6H, q, J 6.6 Hz), 4.70 (0.4H, q, J 6.6 Hz), 3.89, 3.88, 3.86, 3.85, 3.84, 3.81 (6H, 6s), 2.51–1.68 (4H, m), 1.55, 1.54 (3H, 2d, J 6.8, 6.8 Hz).

delta$_C$ (62.90 MHz, CDCl$_3$) 152.30, 152.21, 148.96, 148.54, 148.41, 138.62, 138.56, 135.24, 134.49, 118.84, 118.24, 110.89, 110.76, 109.54, 109.07, 108.98, 102.97, 101.62, 101.31, 92.29, 82.96, 79.37, 62.77, 61.43, 61.18, 55.85, 55.73, 33.82, 32.71, 32.66, 32.44, 32.32, 22.20, 22.11, 22.73.

EXAMPLE 12

O-(1-Methyl-3-(3-pyridyl)propyl)-5-(3,4-dimethoxyphenyl)-gamma-butyrolactol ether

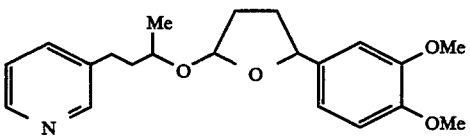

O-(1-Methyl-3-(3-pyridyl)propyl)-5-(3,4-dimethoxyphenyl)-gamma-butyrolactol ether was prepared by the method of Example 1(d) starting from 4-(3-pyridyl)-2-butanol (obtained by catalytic hydrogenation of 1-methyl-3-(3-pyridyl)-1-prop-2-ynol).

60:40 Mixture of 2 diastereoisomers: Colourless oil.

delta$_H$ (250 MHz, CDCl$_3$) 8.40 (2H, br m), 7.45 (1H, m), 7.14 (1H, m), 6.87–6.72 (3H, m), 5.42 (0.6H, dd, J 5.3, 1.8 Hz, CHOO), 5.34 (0.4H, dd, J 5.2, 1.8 Hz, CHOO), 4.99 (1H, t, J 7.2 Hz, OCHAr), 3.87, 3.80, 3.79

(6H, 3s), 3.75 (1H, m), 2.91–1.60 (8H, m), 1.23 (1.2H, d, J 6.1 Hz), 1.13 (1.8H, d, J 6.2 Hz).

delta$_C$ (62.90 MHz, CDCl$_3$) 149.83, 149.77, 148.89, 148.26, 147.15, 147.04, 135.68, 135.54, 134.90, 134.81, 123.40, 118.10, 110.92, 108.95, 104.21, 101.37, 79.05, 73.32, 70.66, 55.79, 38.73, 37.98, 32.75, 32.69, 32.62, 32.57, 29.00, 28.90, 21.89, 19.39.

EXAMPLE 13

O-(3-(3-Pyridyl)propyl)-5-(4-methoxyphenyl)-gamma-butyrolactol ether

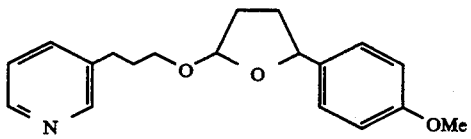

(a) 2-(4-Methoxyphenyl)-5-methoxytetrahydrofuran

Utilising the procedure described in Example 1(b) employing 4-bromoanisole in lieu of 4-bromoveratrole gave 2-(4-methoxyphenyl)-5-methoxytetrahydrofuran (81% yield) as a colourless oil.

delta$_H$ (250 MHz, CDCl$_3$) 7.33 (2H, 2d), 6.90 (2H, 2d), 5.25 (0.5H, dd), 5.10–4.95 (1.5H, m), 3.79 (3H, s), 3.45, 3.43 (3H, 2s), 2.45–1.68 (4H, m).

(b) 2-Benzenesulphonyl-5-(4-methoxyphenyl)tetrahydrofuran

Utilising the procedure described in Example 1(c) employing 2-(4-methoxyphenyl)-5-methoxytetrahydrofuran in lieu of 2-(3,4-dimethoxyphenyl)-5-methoxytetrahydrofuran gave 2-benzenesulphonyl-5-(4-methoxyphenyl)tetrahydrofuran (33% yield) as a white crystalline solid.

delta$_H$ (250 MHz, CDCl$_3$) 7.96 (2H, m), 7.73–7.44 (4H, m), 7.23 (1H, d), 6.90 (2H, m), 5.35 (0.5H, dd), 5.15 (0.5H, dd), 4.99 (1H, dd), 3.85, 3.80 (3H, 2s), 3.03–2.83 (4H, m).

(c) O-(3-(3-Pyridyl)propyl)-5-(4-methoxyphenyl)-gamma-butyrolactol ether

O-(3-(3-Pyridyl)propyl)-5-(4-methoxyphenyl)-gamma-butyrolactol ether was prepared by the procedure described in Example 1(d) employing 2-benzenesulphonyl-5-(4-methoxyphenyl)tetrahydrofuran in lieu of 2-benzenesulphonyl-5-(3,4-dimethoxyphenyl)tetrahydrofuran.

Fraction A (trans diastereoisomer): Yellow oil.

delta$_H$ (250 MHz, CDCl$_3$) 8.47 (1H, d, J 1.6 Hz), 8.44 (1H, dd, J 4.8, 1.5 Hz), 7.51 (1H, dt, J 7.8, 1.6 Hz), 7.26 (2H, d, J 8.6 Hz), 7.19 (1H, dd, J 7.8, 4.9 Hz), 6.87 (2H, d, J 8.7 Hz), 5.31 (1H, dd, J 5.3, 2.0 Hz, CHOO), 5.03 (1H, t, J 7.2 Hz, OCHAr), 3.79 (3H, s), 3.79 (1H, dt, J 9.7, 6.3 Hz), 3.44 (1H, dt, J 9.8, 6.3 Hz), 2.71 (2H, t, J 7.7 Hz), 2.45–1.66 (6H, m).

delta$_C$ (62.90 MHz, CDCl$_3$) 158.94, 149.94, 147.26, 137.12, 135.77, 134.21, 127.12, 123.16, 113.70, 104.26, 79.02, 66.31, 55.19, 32.66, 32.50, 30.97, 29.53.

Fraction B (20:80 mixture of trans and cis diastereoisomers): Yellow oil.

delta$_H$ (250 MHz, CDCl$_3$) 8.46 (1H, d, J 1.0 Hz), 8.43 (1H, d, J 4.8 Hz), 7.76–7.42 (1H, m), 7.29 (2H, d, 8.7 Hz), 7.17 (1H, dd, J 7.7, 5.0 Hz), 6.85 (2H, d, J 8.7 Hz), 5.31 (0.2H, dd, 5.3, 2.0 Hz, CHOO), 5.15 (0.8H, d, J 3.7 Hz, CHOO), 4.95 (1H, m, OCHAr), 3.81 (1H, m), 3.78 (3H, s), 3.40 (1H, m), 2.68 (2H, m), 2.42–1.66 (6H, m).

delta$_C$ (62.90 MHz, CDCl$_3$) 158.91, 149.86, 149.78, 147.49, 147.20, 137.15, 135.76, 135.03, 132.11, 129.01, 127.63, 127.10, 125.07, 123.24, 123.19, 113.70, 113.61, 104.25, 104.03, 82.37, 66.28, 66.16, 63.09, 55.17, 33.85, 32.68, 32.50, 30.88, 29.56, 28.99.

EXAMPLE 14

O-(3-(3-Pyridyl)propyl)-5-(3,4,5-trimethoxyphenyl)-gamma-butyrolactol ether

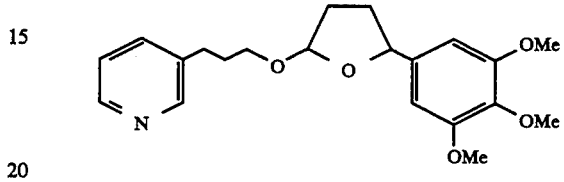

(a) 2-(3,4,5-Trimethoxyphenyl)-5-methoxytetrahydrofuran

To stirred solution of 1-bromo-3,4,5-trimethoxybenzene (2.47 g, 10 mmol) in THF (20 ml) at −78° C. was added 2.5M n-butyllithium in hexane (4.4 ml, 11 mmol). After 0.75 h the solution was cannulated into a mixture of 1M zinc(II) bromide in THF (11 ml, 11 mmol) and magnesium(II) bromide etherate (2.86 g, 15 mmol) in THF (10 ml) at −78° C. The resulting mixture was allowed to warm to room temperature over 1 h and then sonicated for 0.4 h. A solution of 2-benzenesulphonyl-5-methoxytetrahydrofuran (1.85 g, 7.5 mmol) in THF (10 ml) was added and the mixture stirred at room temperature for 1 h, sonicated for 1 h and stirred overnight. The reaction was quenched by the addition of aqueous ammonium chloride (20 ml). Work up and purification as described for Example 1(b) gave 2-(3,4,5-trimethoxyphenyl)-5-methoxytetrahydrofuran (0.55 g, 27%) as a colourless oil.

(b) 5-(3,4,5-Trimethoxyphenyl)-gamma-butyrolactol

To a stirred solution of 2-(3,4,5-trimethoxyphenyl)-5-methoxytetrahydrofuran (0.5 g, 1.87 mmol) in THF (10 ml) at room temperature was added 1M HCl (5 ml). After 5 h the reaction mixture was partitioned between water (10 ml) and diethyl ether (20 ml). The aqueous phase was extracted with diethyl ether (2×10 ml). The combined organics were dried over anhydrous sodium sulphate, filtered and evaporated to give a yellow oil. Column chromatography (flash silica gel; ethyl acetate) gave 3,4,5-trimethoxyphenyl)-gamma-butyrolactol (0.3 g, 63%) as a white solid.

mp 82° C.

i.r. (KBr) 3400, 2970, 1590, 1470 cm$^{-1}$ delta$_H$ (250 MHz, CDCl$_3$) 6.69 (0.9H, s), 6.55 (1.1H, s), 5.78 (0.55H, dt, J 5.1, J 2.6 Hz), 5.64 (0.45H, br m), 5.18 (0.55 H, t, J 7.0 Hz), 4.95 (0.45H, t, J 7.4 Hz), 3.87 (6H, s), 3.84 (3H, s), 3.03 (0.45H, d, J 3.4 Hz), 2.88 (0.55H, d, J 3.0 Hz), 2.50–1.73 (4H, m)

(c) O-(3-(3-Pyridyl)propyl)-5-(3,4,5-trimethoxyphenyl)-gamma-butyrolactol ether

A mixture of 5-(3,4,5-trimethoxyphenyl)-gamma-butyrolactol (100 mg, 0.39 mmol), benzenesulphinic acid (61 mg, 0.43 mmol) and powdered calcium chloride (200 mg, 1.8 mmol) in THF (5 ml) was stirred at room temperature overnight. 3-(3-Pyridyl)-1-propanol (0.10 ml, 0.78 mmol) and magnesium(II) bromide etherate (200 mg, 0.78 mmol) were added and the suspension stirred, with occasional sonication, at room temperature for 24 h. Aqueous ammonium chloride (10 ml) was added and the mixture extracted with DCM (3×10 ml), the combined organics dried over anhydrous sodium sulphate, filtered and evaporated to give an oil. Column chromatography (flash silica gel, ethyl acetate) gave O-(3-(3-pyridyl)propyl)-5-(3,4,5-trimethoxyphenyl)-gamma-butyrolactol ether.

Fraction A (trans diastereoisomer) (45 mg, 31% yield): Colourless oil.

$\delta_H$(250 MHz, CDCl$_3$) 8.46 (1H, br s), 8.42 (1H, d, J 4.6 Hz), 7.50 (1H, dt, J 7.9, 1.4 Hz), 7.18 (1H, dd, J 7.4, 4.8 Hz), 6.54 (2H, s), 5.31 (1H, dd, J 5.2, 1.9 Hz, CHOO), 4.99 (1H, t, J 7.0 Hz, OCHAr), 3.85 (6H, s), 3.81 (3H, s), 2.75 (1H, dt, J 9.7, 6.3 Hz), 3.45 (1H, dt, J 9.7, 6.3 Hz), 2.70 (2H, t, J 7.6 Hz), 2.40–1.73 (6H, m).

$\delta_C$ (62.9 MHz, CDCl$_3$) 153.15, 149.89, 147.23, 137.09, 135.77, 123.19, 104.31, 102.66, 79.33, 66.31, 60.70, 55.98, 32.78, 32.35, 30.90, 29.50.

Fraction B (cis diastereoisomer) (20 mg, 14% yield): Colourless oil.

$\delta_H$(250 MHz, CDCl$_3$) 8.45 (2H, br m), 7.46 (1H, br d, J 7.5 Hz), 7.20 (1H, dd, J 7.3, 5.0 Hz), 6.62 (2H, s), 5.18 (1H, br d, J 2.9 Hz), 4.94 (1H, t, J 7.0 Hz), 3.85 (1H, m), 3.83 (6H, s), 3.82 (3H, s), 3.48 (1H, m), 2.70 (2H, t, J 7.6 Hz), 2.08–1.88 (6H, br m).

$\delta_C$ (62.9 MHz, CDCl$_3$) 153.08, 149.79, 147.36, 138.61, 136.90, 135.77, 123.26, 104.34, 103.25, 82.86, 66.43, 60.71, 55.92, 33.72, 32.78, 30.99, 30.91.

EXAMPLE 15

O-(3-(3-Pyridyl)propyl)-5-(4-fluorophenyl)-gamma-butyrolactol ether

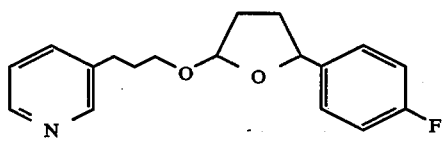

(a) 5-(4-Fluorophenyl)-gamma-butyrolactol

A 1.5M solution of diisobutylaluminium hydride in toluene (7.5 ml, 11.3 mmol) was added dropwise to a stirred solution of 5-(4-fluorophenyl)-gamma-butyrolactone (2.0 g, 11.1 mmol) in toluene (40 ml) at −78° C. under argon. The mixture was stirred for 2 h at −78° C., water (0.5 ml), 1M aqueous sodium hydroxide (0.5 ml) and water (1.5 ml) added sequentially over 0.5 h. The mixture was stirred until a granular precipitate formed which was removed by filtration through celite. The celite was washed with ethyl acetate and the combined organics concentrated to give 5-(4-fluorophenyl)-gamma-butyrolactol (1.8 g, 89%; 1:1 mixture of cis and trans diastereoisomers) as a clear oil which was used directly in the next step.

$\delta_H$(250 MHz, CDCl$_3$) 7.47 (4H, m), 5.71 (0.5H, t, J 2.4 Hz), 5.58 (0.5H, s), 5.21 (0.5H, t, J 7.0 Hz), 4.97 (0.5H, t, J 7.5 Hz), 4.1 (0.5H, s), 4.04 (0.5H, s), 2.55–1.65 (4H, m).

(b) O-(3-(3-Pyridyl)propyl)-5-(4-fluorophenyl)-gamma-butyrolactol ether

Trifluoracetic anhydride (0.77 ml, 5.5 mmol) was added dropwise to a stirred mixture of 5-(4-fluorophenyl)-gamma-butyrolactol (1.0 g, 5.5 mmol) and triethylamine (0.77 ml, 0.55 mmol) in dry DCM (50 ml) at −78° C. under argon. The mixture was stirred at −78° C. for 3 h and 3-(3-pyridyl)propan-1-ol (2.2 ml, 16.5 mmol) added dropwise. The mixture was allowed to warm slowly to room temperature and stirred overnight. Aqueous sodium hydrogen carbonate (50 ml) was added and the organic layer separated, dried over anhydrous sodium sulphate, filtered and concentrated. Column chromatography (flash silica gel; ethyl acetate) gave trans-O-(3-(3-pyridyl)propyl)-5-(4-fluorophenyl)-gamma-butyrolactol ether (0.14 g, 8%) followed by cis-O-(3-(3-pyridyl)propyl)-5-(4-fluorophenyl)-gamma-butyro-lactol ether (0.18 g, 11%).

Fraction A (trans diastereoisomer): Pale yellow oil.

$\delta_H$(250 MHz, CDCl$_3$) 8.45 (1H, d, J 1.6 Hz), 8.41 (1H, dd, J 4.7, 1.3 Hz), 7.48 (1H, dt, J 7.8, 1.9 Hz), 7.27 (2H, m), 7.16 (1H, dd, J 7.7, 4.8 Hz), 6.99 (2H, m), 5.29 (1H, dd, J 5.3, 1.9 Hz, CHOO), 5.03 (1H, t, J 7.2 Hz, OCHAr), 3.76 (1H, dt, J 9.8, 6.4 Hz), 3.43 (1H, dt, J 9.8, 6.4 Hz), 2.96 (2H, t, J 7.7 Hz), 2.45–1.60 (6H, m).

$\delta_C$ (62.90 MHz, CDCl$_3$) 162.07 (d, J 239.6 Hz), 149.92, 147.26, 138.02, 137.08, 135.7, 127.38 (d, J 7.7 Hz), 123.16, 115.07 (d, J 21.3 Hz), 104.35, 78.65, 66.37, 32.79, 32.35, 30.91, 29.52.

Fraction B (cis diastereoisomer): Pale yellow oil.

$\delta_H$(250 MHz, CDCl$_3$) 8.41 (1H, d, J 1.9 Hz), 8.38 (1H, dd, J 4.8, 1.5 Hz), 7.43 (1H, dt, J 7.8, 1.7 Hz), 7.26 (2H, m), 7.12 (1H, ddd, J 7.8, 4.8, 0.6 Hz), 6.95 (2H, m), 5.11 (1H, d, J 3.2 Hz, CHOO), 4.92 (1H, m, OCHAr), 3.77 (1H, dt, J 9.7, 6.3 Hz), 3.38 (1H, dt, J 9.7, 6.4 Hz), 2.64 (2H, t, J 7.7 Hz), 2.22–1.80 (6H, m).

$\delta_C$ (62.90 MHz, CDCl$_3$) 162.20 (d, J 251.6 Hz), 149.86, 147.26, 138.87, 137.12, 135.71, 127.88 (d, J 8.0 Hz), 123.12, 115.00 (d, J 21.6 Hz), 104.25, 81.93, 66.30, 33.76, 32.84, 30.85, 29.53.

EXAMPLE 16

O-(3-(3-Pyridyl)propyl)-5-(4-chlorophenyl)-gamma-butyrolactol ether

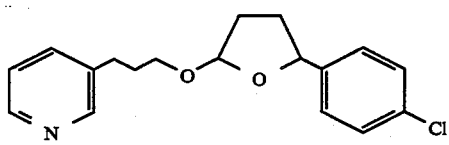

(a) Methyl 3-(4-chlorobenzoyl)propionate

Thionyl chloride (2.4 ml, 33 mmol) was added dropwise to a stirred solution of 3-(4-chlorobenzoyl)propionic acid (5.0 g, 24 mmol) in dry methanol (50 ml) at 0° C. The mixture was heated at reflux for 2 h, cooled and the solvent removed under reduced pressure to give methyl 3-(4-chlorobenzoyl)propionate (5.3 g, 97%) as a colourless oil. $\delta_H$ (250 MHz, CDCl$_3$) 7.93 (2H, d, J 8.5 Hz), 7.45 (2H, d, J 8.6 Hz), 3.72 (3H, s), 3.29 (2H, t, J 6.6 Hz), 2.78 (2H, t, J 6.6 Hz).

(b) 5-(4-Chlorophenyl)-gamma-butyrolactone

Sodium borohydride (1.3 g, 35 mmol) was added portionwise to a stirred solution of methyl 3-(4-chlorobenzoyl)propionate (5.3 g, 23 mmol) in methanol (50 ml) at 0° C. The mixture was allowed to warm up to room temperature, stirred for 4 h and partitioned between 1M aqueous hydrochloric acid (100 ml) and DCM (150 ml). The organic layer was separated and the aqueous layer extracted with DCM 2×100 ml). The combined extracts were dried over anhydrous sodium sulphate, filtered and concentrated to give crude methyl 4-(4-chlorophenyl)-4-hydroxybutanoate which was dissolved in methanol (40 ml). Sodium hydride (80% dispersion in oil: 100 mg, 3 mmol) was added, the mixture stirred for 1 h, and partitioned between aqueous 1M hydrochloric acid (50 ml) and ethyl acetate (100 ml). The organic layer was separated and the aqueous layer extracted with ethyl acetate (100 ml). The combined organics were dried over anhydrous potassium carbonate, filtered and concentrated to give 5-(4-chlorophenyl)-gamma-butyrolactone (3.85 g, 83%) as a colourless oil.

delta$_H$ (250 MHz, CDCl$_3$) 7.40–7.20 (4H, m), 5.46 (1H, dd, J 8.2, 6.1 Hz), 2.70–2.60 (3H, m), 2.13 (1H, m).

(c) O-(3-(3-Pyridyl)propyl)-5-(4-chlorophenyl)-gamma-butyrolactol ether

O-(3-(3-Pyridyl)propyl)-5-(4-chlorophenyl)-gamma-butyrolactol ether was prepared by the procedure described in Example 15 employing 5-(4-chlorophenyl)-gamma-butyrolactone as starting material.

Fraction A (trans diastereoisomer) (20% yield for last step after chromatography): Yellow oil.

delta$_H$ (250 MHz, CDCl$_3$) 8.47 (1H, s), 8.43 (1H, d, J 4.8 Hz), 7.50 (1H, dt, J 7.7, 1.8 Hz), 7.28 (4H, m), 7.19 (1H, dd, J 7.7, 4.9 Hz), 5.31 (1H, dd, J 5.2, 1.8 Hz, CHOO), 5.04 (1H, t, J 7.1 Hz, OCHAr), 3.78 (1H, dt, J 9.7, 6.4 Hz), 3.45 (1H, dt, J 9.7, 6.4 Hz), 2.71 (2H, t, J 7.6 Hz), 2.42 (1H, m), 2.17 (1H, m), 2.05–2.85 (3H, m), 1.71 (1H, m).

delta$_C$ (62.90 MHz, CDCl$_3$) 149.83, 147.16, 140.94, 137.09, 135.81, 132.89, 128.39, 127.07, 123.19, 104.41, 78.55, 66.34, 32.73, 32.25, 30.90, 29.50.

Fraction B (cis diastereoisomer) (20% yield for last step after chromatography): Yellow oil.

delta$_H$ (250 MHz, CDCl$_3$) 8.45 (2H, br s), 7.48 (1H, br d, J 7.5 Hz), 7.28 (4H, m), 7.19 (1H, dd, J 7.7, 4.9 Hz), 5.17 (1H, d, J 3.4 Hz, CHOO), 4.97 (1H, m, OCHAr), 3.81 (1H, dt, J 9.6, 6.1 Hz), 3.43 (1H, dt, J 9.7, 6.4 Hz), 2.69 (2H, t, J 7.6 Hz), 2.35–1.85 (6H, m).

delta$_C$ (62.90 MHz, CDCl$_3$) 149.86, 147.29, 141.79, 137.00, 135.68, 132.86, 128.33, 127.60, 123.17, 104.31, 81.78, 66.31, 33.67, 32.76, 30.82, 29.51.

EXAMPLE 17

O-(3-(3-Pyridyl)propyl)-5-(4-bromophenyl)-gamma-butyrolactol ether

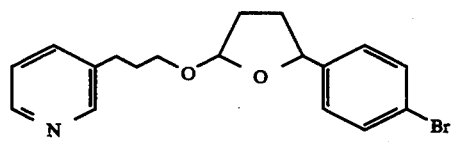

O-(3-(3-Pyridyl)propyl)-5-(4-bromophenyl)-gamma-butyrolactol ether was prepared by the procedure described in Example 16 employing 3-(4-bromobenzoyl)-propionic acid as starting material.

Fraction A (trans diastereoisomer) (29% for last step after chromatography): Yellow oil.

delta$_H$ (250 MHz, CDCl$_3$) 8.47 (1H, d, J 1.7 Hz), 8.44 (1H, dt, J 4.8, 1.5 Hz), 7.52 (1H, dt, J 7.8, 1.9 Hz), 7.46 (2H, d, J 8.5 Hz), 7.33–7.15 (3H, m), 5.32 (1H, dd, J 5.2, 1.8 Hz, CHOO), 5.04 (1H, t, J 7.1 Hz, OCHAr), 7.78 (1H, dt, J 9.7, 6.4 Hz), 3.46 (1H, dt, J 9.7, 6.3 Hz), 2.72 (2H, t, J 7.7 Hz), 2.45 (1H, m), 2.18 (1H, m), 2.08–1.87 (3H, m), 1.74 (1H, m).

delta$_C$ (62.90 MHz, CDCl$_3$) 149.81, 147.14, 141.42, 135.64, 131.22, 127.33, 123.08, 120.89, 104.32, 78.47, 66.26, 32.61, 32.14, 30.80, 29.42.

Fraction B (cis diastereoisomer) (21% yield for last step after chromatography): Yellow oil.

delta$_H$ (250 MHz, CDCl$_3$) 8.45 (1H, d, J 2.5 Hz), 8.43 (1H, dd, J 4.9, 1.6 Hz), 7.48 (1H, dt, J 7.8, 2.0 Hz), 7.43 (2H, d, J 8.5 Hz), 7.22 (2H, d, J 8.8 Hz), 7.18 (1H, dd, J 7.8, 4.5 Hz), 5.16 (1H, dd, J 4.1, 1.5 Hz, CHOO), 4.95 (1H, dd, J 8.9, 6.5 Hz, OCHAr), 3.81 (1H, dt, J 9.7, 6.3 Hz), 3.42 (1H, dt, J 9.7, 6.5 Hz), 2.68 (2H, t, J 7.7 Hz), 2.26 (1H, m), 2.12–1.84 (5H, m).

delta$_C$ (62.90 MHz, CDCl$_3$) 149.82, 147.21, 142.27, 136.95, 135.66, 131.22, 127.90, 123.14, 120.95, 104.30, 81.73, 66.26, 33.65, 32.67, 30.77, 29.48.

EXAMPLE 18

O-(3-(3-Pyridyl)propyl)-5-(3,4-dichlorophenyl)-gamma-butyrolactol ether

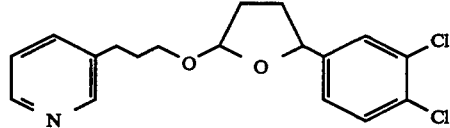

O-(3-(3-Pyridyl)propyl)-5-(3,4-dichlorophenyl)-gamma-butyrolactol ether was prepared by the procedure described in Example 16 employing 3-(3,4-dichlorobenzoyl)propionic acid as starting material.

Fraction A (trans diastereoisomer) (15% yield for last step after chromatography): Yellow oil.

delta$_H$ (250 MHz, CDCl$_3$) 8.46 (2H, br s), 7.50 (1H, dt, J 7.8, 1.6 Hz), 7.39 (2H, m), 7.19 (1H, dd, J 7.7, 4.8 Hz), 7.14 (1H, dd, J 8.3, 1.9 Hz), 5.31 (1H, dd, 5.2, 1.9 Hz, CHOO), 5.02 (1H, t, J 7.1 Hz, OCHAr), 3.76 (1H, dt, J 9.8, 6.4 Hz), 3.45 (1H, dt, J 9.7, 6.4 Hz), 2.70 (2H, t, J 7.7 Hz), 2.43 (1H, m), 2.14 (1H, m), 2.05–1.85 (3H, m), 1.43 (1H, m).

delta$_C$ (62.90 MHz, CDCl$_3$) 149.93, 147.30, 142.93, 137.08, 135.76, 130.24, 127.67, 125.05, 123.22, 104.49, 77.99, 66.47, 32.70, 32.14, 30.89, 29.54.

Fraction B (cis diastereoisomer) (14% yield for last step after chromatography): Yellow oil.

delta$_H$ (250 MHz, CDCl$_3$) 8.46 (1H, d, J 2.0 Hz), 8.43 (1H, dd, J 4.8, 1.5 Hz), 7.49 (2H, m), 7.36 (1H, d, J 8.2 Hz), 7.18 (1H, dd, J 7.8, 4.9 Hz), 7.15 (1H, dd, 8.2, 2.1 Hz), 5.16 (1H, dd, J 4.3, 1.7 Hz, CHOO), 4.95 (1H, dd, J 8.8, 6.7 Hz, OCHAr), 3.83 (1H, dt, J 9.7, 6.3 Hz), 3.44 (1H, dt, J 9.6, 6.5 Hz), 2.71 (2H, t, J 7.7 Hz), 2.29 (1H, m), 2.15–1.85 (5H, m).

delta$_C$ (62.90 MHz, CDCl$_3$) 149.88, 147.31, 143.89, 136.97, 135.63, 130.12, 128.28, 125.54, 123.17, 104.48, 81.13, 66.54, 33.60, 32.74, 30.81, 29.60.

EXAMPLE 19

O-(3-(3-Pyridyl)propyl)-5-(3-chloro-4-methoxyphenyl)-gamma-butyrolactol ether

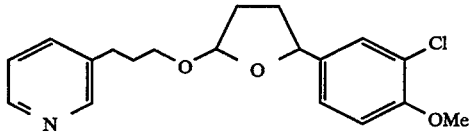

O-(3-(3-Pyridyl)propyl)-5-(3-chloro-4-methoxyphenyl)-gamma-butyrolactol ether was prepared by the procedure described in Example 16 employing 3-(3-chloro-4-methoxybenzoyl)propionic acid as starting material.

1:1 Mixture of trans and cis diastereoisomers (56% yield for last step after chromatography): Yellow oil.

$\delta_H$ (250 MHz, CDCl$_3$) 8.43 (2H, m), 7.48 (1H, d, J 7.8 Hz), 7.41 (0.5H, d, J 2.2 Hz), 7.32 (0.5H, d, J 2.2 Hz), 7.15 (2H, m), 6.86 (0.5 H, d, J 8.5 Hz), 6.83 (0.5 H, d, J 8.5 Hz), 5.27 (0.5H, dd, 5.3, 1.9 Hz, CHOO), 5.13 (0.5H, d, J 3.5 Hz, CHOO), 4.98 (1H, m, OCHAr), 3.84 (3H, s), 3.79 (1H, m), 3.42 (1H, m), 2.69 (2H, m), 2.45–1.60 (6H, m).

$\delta_C$ (62.90 MHz, CDCl$_3$) 154.10, 149.76, 147.11, 137.07, 136.44, 135.71, 135.47, 128.31, 127.65, 125.68, 125.15, 123.14, 122.24, 111.76, 111.60, 104.26, 104.13, 81.56, 78.28, 66.28, 56.03, 33.68, 32.64, 32.25, 30.82, 29.55, 29.44.

EXAMPLE 20

O-(3-(3-Pyridyl)propyl)-5-phenyl-gamma-butyrolactol ether

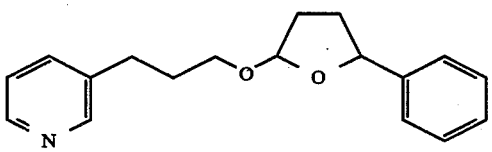

O-(3-(3-Pyridyl)propyl)-5-phenyl-gamma-butyrolactol ether was prepared by the procedure described in Example 15 employing 5-phenyl-gamma-butyrolactone as starting material.

Fraction A (trans diastereoisomer): Yellow oil.

$\delta_H$ (250 MHz, CDCl$_3$) 8.47 (1H, d J 1.9 Hz), 8.42 (1H, dd, J 4.8, 1.6 Hz), 7.49 (1H, dt, J 7.8, 2.2 Hz), 7.45–7.13 (6H, m), 5.32 (1H, dd, J 5.3, 1.9 Hz, CHOO), 5.08 (1H, t, J 7.2 Hz, OCHAr), 3.78 (1H, dt, J 9.8, 6.3 Hz), 3.45 (1H, dt, J 9.8, 6.4 Hz), 2.70 (2H, t, J 7.7 Hz), 2.42 (1H, m), 2.16 (1H, m), 2.04–1.84 (3H, m), 1.76 (1H, m).

$\delta_C$ (62.90 MHz, CDCl$_3$) 149.59, 146.89, 142.03, 135.42, 127.94, 126.96, 125.40, 122.83, 104.06, 78.95, 65.96, 32.37, 32.03, 30.62, 29.21.

EXAMPLE 21

O-(2-Hydroxy-3-(3-pyridyl)propyl)-5-(3,4-dichlorophenyl)-gamma-butyrolactol ether

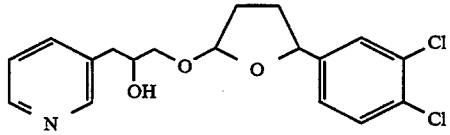

O-(2-Hydroxy-3-(3-pyridyl)propyl)-5-(3,4-dichlorophenyl)-gamma-butyrolactol ether was prepared by the procedure described in Example 18 employing 2-hydroxy-3-(3-pyridyl)-1-propanol in lieu of 3-(3-pyridyl)-1-propanol.

Mixture of diastereoisomers: Yellow oil.

$\delta_H$ (250 MHz, CDCl$_3$): 8.47 (2H, br s), 7.56–7.05 (5H, m), 5.38–4.86 (2H, m), 3.83 (1H, m), 3.63–3.53 (3H, m), 2.78 (2H, dd, J 5.9, 5.6 Hz), 2.46–1.62 (4H, m).

EXAMPLE 22

O-(3-(3-Pyridyl)propyl)-3-methyl-5-(3,4-dimethoxyphenyl)-gamma-butyrolactol ether

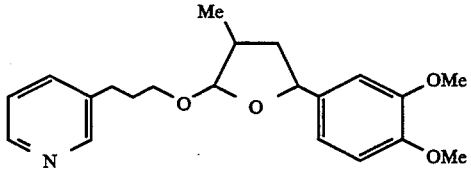

(a) 5-(3,4-Dimethoxyphenyl)-gamma-butyrolactone 5-(3,4-Dimethoxyphenyl)-gamma-butyrolactone was prepared by the procedure described in Example 16(a) and (b) employing 3-(3,4-dimethoxybenzoyl)propionic acid as starting material.

$\delta_H$ (250 MHz, CDCl$_3$) 6.86 (3H, m), 5.43 (1H, dd, J 7.3, 5.6 Hz), 3.87 (3H, s), 3.86 (3H, s), 2.70–2.10 (4H, m).

(b) 3-Methyl-5-(3,4-dimethoxyphenyl)-gamma-butyrolactone

A solution of lithium diisopropylamide was prepared by treating diisopropylamine (240 µl, 1.7 mmol) in dry THF (4 ml) at −78° C. under argon with 1.6M n-butyllithium in hexane (1.07 ml, 1.7 mmol) and allowing the mixture to warm up to −20° C. The solution was added to a stirred solution of 5-(3,4-dimethoxyphenyl)-gamma-butyrolactone (0.38 g, 1.7 mmol) in dry THF (10 ml) at −78° C. After 15 min an excess of methyl iodide was added (1.5 ml). The reaction mixture was allowed to warm to room temperature over 2 h, and treated with aqueous ammonium chloride (30 ml) and ethyl acetate (30 ml). The organics were separated, washed with brine, dried over anhydrous sodium sulphate, filtered and concentrated. Column chromatography (flash silica gel; 1:1 ethyl acetate/hexane) gave one diastereoisomer of 3-methyl-5-(3,4-dimethoxyphenyl)-gamma-butyrolactone (0.17 g, 42%) as a colourless oil.

$\delta_H$ (250 MHz, CDCl$_3$) 6.80 (3H, m), 5.49 (1H, dd, J 7.3, 5.2 Hz), 3.84 (3H, s), 3.83 (3H, s), 2.72 (1H, m), 2.50–2.10 (2H, m), 1.30 (3H, d, J 7.3 Hz).

(c) O-(3-(3-Pyridyl)propyl)-3-methyl-5-(3,4-dimethoxyphenyl)-gamma-butyrolactol ether O-(3-(3-Pyridyl)propyl)-3-methyl-5-(3,4-dimethoxyphenyl)-gamma-butyrolactol ether was prepared by the procedure described in Example 15 employing 3-methyl-5-(3,4-dimethoxyphenyl)-gamma-butyrolactone as starting material.

Mixture of diastereoisomers (2% yield for last step after chromatography): Yellow oil.

delta$_H$ (250 MHz, CDCl$_3$) 8.50–8.40 (2H, m), 7.60–7.45 (1H, m), 7.30–7.19 (1H, m), 7.00–6.80 (3H, m), 5.20–5.08 (2H, m), 3.93–3.82 (6H, m), 3.84–3.78 (1H, m), 3.50–3.39 (1H, m), 2.80–2.70 (2H, dd, J 15.2, 7.5 Hz), 2.48–1.88 (5H, m), 1.12 (1.5H, d, J 6.7 Hz), 1.09 (1.5H, d, J 6.5 Hz).

EXAMPLE 23

O-((4-(1H-2-Methylbenzimidazyl)phenyl)methyl)-5-(3,4-dimethoxyphenyl)-gamma-butyrolactol ether

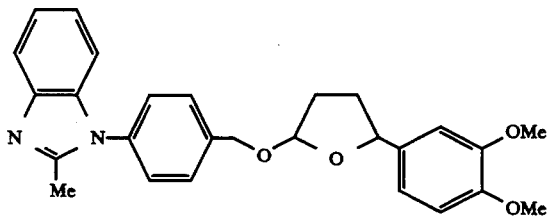

(a) N-(Ethyl-4-benzoate)-2-nitroaniline

A mixture of 2-fluoronitrobenzene (30.0 g, 0.21 mol), ethyl 4-aminobenzoate (52.53 g, 0.32 mol) and potassium fluoride (12.32 g, 0.21 mol) was heated at 180° C. for 48 h. The reaction mixture was allowed to cool, ethyl acetate (500 ml) added, and the mixture washed consecutively with water (2×100 ml), 2M aqueous potassium hydroxide (100 ml) and saturated brine (100 ml). The organics were dried over anhydrous magnesium sulphate, filtered and concentrated to give an orange solid, which was recrystalised from DIPE to give N-(ethyl-4-benzoate)-2-nitroaniline (13.51 g, 22%) as an orange crystalline solid.

delta$_H$ (250 MHz, CDCl$_3$) 9.49 (1H, br s), 8.20 (1H, dd, J 8.6, 0.9 Hz), 8.06 (2H, dd, J 8.7, 2.0 Hz), 7.45 (2H, m), 7.32–7.27 (3H, m), 4.38 (2H, q, J 7.1 Hz), 1.40 (3H, t, J 7.1 Hz).

(b) N-(Ethyl-4-benzoate)-1,2-diaminobenzene

A solution of sodium dithionite (39.61 g, 0.194 mol) in water (175 ml) was added to a suspension of N-(ethyl-4-benzoate)-2-nitroaniline (13.51 g, 0.047 mol) in ethanol (600 ml). The mixture was heated under reflux for 0.75 h, cooled, treated with dilute aqueous ammonia (400 ml) and concentrated under reduced pressure. The resulting slurry was treated with dilute aqueous ammonia (300 ml), filtered and washed with water (200 ml). The solid was freeze dried to give N-(ethyl-4-benzoate)-1,2-diaminobenzene (8.56 g, 71%) as a white solid.

delta$_H$ (250 MHz, CDCl$_3$) 7.87 (2H, d, J 8.6 Hz), 7.55–6.46 (6H, br m), 5.57 (1H, s, NH), 4.32 (2H, q, J 7.1 Hz), 4.10 (2H, d, J 6.7 Hz), 1.36 (3H, t, J 7.1 Hz).

(c) Ethyl 4-(1H-2-methylbenzimidazyl)benzoate

To a suspension of N-(ethyl-4-benzoate)-1,2-diaminobenzene (8.56 g, 0.0033 mol) in absolute ethanol (45 ml) was added ethyl acetimidate hydrochloride (12.36 g, 0.1 mol) at 0° C. The mixture was stirred at room temperature for 2 h and ice cold aqueous 2M potassium hydroxide (40 ml) added. The product was extracted into ethyl acetate (2×100 ml), washed with water (3×100 ml), dried over anhydrous magnesium sulphate and concentrated. Crystallisation of the product from ether gave ethyl 4-(1H-2-methylbenzimidazyl)benzoate (1.5 g, 16%) as an off white crystalline solid.

delta$_H$ (250 MHz, CDCl$_3$) 8.28 (2H, d, J 8.6 Hz), 7.76 (1H, d, J 7.3 Hz), 7.48 (2H, d, J 8.6 Hz), 7.32–7.11 (3H, m), 4.45 (2H, q, J 7.1 Hz), 2.55 (3H, s), 1.45 (3H, t, J 7.1 Hz).

(d) 4-(1H-2-Methylbenzimidazyl)phenylmethanol

Ethyl 4-(1H-2-methylbenzimidazyl)benzoate (0.43 g, 1.54 mmol) was added to a stirred solution of lithium aluminium hydride (0.07 g, 1.84 mmol) in anhydrous THF at −20° C. The mixture was allowed to warm to room temperature and was stirred overnight under argon. The reaction was quenched by alternate dropwise additions of 10% sodium hydroxide (5 ml) and water (5 ml). The aqueous phase was separated and extracted with DCM (3×20 ml). The combined organics were washed with water (20 ml), dried over anhydrous potassium carbonate and evaporated to give crude 4-(1H-2-methylbenzimidazyl)phenylmethanol (0.36 g, 97%) as an off white amorphous solid which was used directly in the next step.

delta$_H$ (250 MHz, CDCl$_3$) 7.69 (1H, d, J 8.0 Hz), 7.61 (2H, d, J 8.2 Hz), 7.33 (2H, d, J 8.2 Hz), 7.27–7.09 (3H, m), 4.88 (2H, s), 2.48 (3H, s).

(e) O-((4-(1H-2-Methylbenzimidazyl)phenyl)methyl)-5-(3,4-dimethoxyphenyl)-gamma-butyrolactol ether O-((4-(1H-2-Methylbenzimidazyl)phenyl)methyl)-5-(3,4-dimethoxyphenyl)-gamma-butyrolactol ether was prepared by the procedure described in Example 1(d) employing 4-(1H-2-methylbenzimidazyl)phenylmethanol in lieu of 3-(3-pyridyl)-1-propanol.

60:40 Mixture of trans and cis diastereoisomers: Yellow foam.

delta$_H$ (250 MHz, CDCl$_3$) 7.76 (1H, d, J 5.6 Hz) 7.59 (1H, dd, J 8.2, 5.9 Hz), 7.36 (2H, dd, J 8.3, 1.6 Hz), 7.26 (4H, m), 6.92 (3H, m), 5.53 (0.6H, dd, J 5.2, 1.8 Hz, CHOO), 5.37 (0.4H, d, J 3.9 Hz, CHOO) 5.10 (0.4H, m, OCHAr), 4.97 (0.6H, t, J 12.0 Hz, OCHAr), 4.68 (2H, dd, J 12.4, 2.7 Hz), 3.92, 3.89, 3.88, 3.78 (6H, 4s), 2.55 (3H, s), 2.49–1.76 (4H, m).

delta$_C$ (62.90 MHz, CDCl$_3$) 151.62, 149.01, 148.45, 142.52, 139.22, 139.09, 136.36, 135.40, 135.13, 134.46, 129.01, 128.74, 126.89, 122.48, 122.28, 118.92, 118.26, 110.98, 110.74, 109.82, 109.77, 109.57, 109.00, 103.94, 103.50, 83.03, 79.46, 68.41, 67.93, 55.85, 55.80, 55.57, 33.97, 32.75, 32.64, 32.54, 14.35.

EXAMPLE 24

O-((4-(1H-2-Methylbenzimidazylmethyl)phenyl)methyl)-5-(3,4-dimethoxyphenyl)-gamma-butyrolactol ether

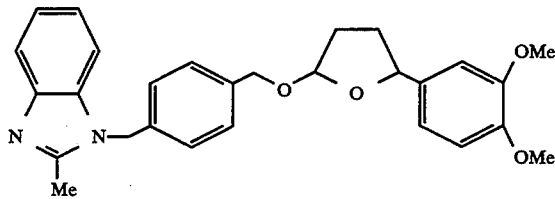

(a) Ethyl 4-bromomethylbenzoate

To a solution of ethyl p-toluate (40.0 g, 0.24 mol) and NBS (43.44 g, 0.24 mol) in carbon tetrachloride (200 ml) heated at reflux was added 2,2'-azobis-(2-methylpropionitrile) (180 mg). The mixture was heated at reflux for 4 h, cooled to room temperature and stirred overnight. The white precipitate of succinimide that formed on the surface of the solution was separated and discarded. The filtrate was concentrated and crystallisation from hexane gave ethyl 4-bromomethylbenzoate (37.23 g, 63%) as an off white crystalline solid.

m.p. 34°–35° C.

i.r. (KBr) 3020, 2980, 1710 cm$^{-1}$ delta$_H$(250 MHz, CDCl$_3$) 8.00 (2H, d, J 8.4 Hz), 7.43 (2H, d, J 8.4 Hz), 4.47 (2H, s), 4.35 (2H, q, J 7.1 Hz), 1.37 (3H, t, J 7.1 Hz).

(b) Ethyl 4-(1H-2-methylbenzimidazylmethyl)benzoate

Sodium hydride (80% dispersion in oil) (0.61 g, 0.02 mol) was added to a stirred solution of 2-methylbenzimidazole (2.00 g, 0.017 mol) in dry THF (30 ml) under argon. After 1.5 h the mixture was cooled to 0° C. and treated with ethyl 4-bromomethylbenzoate (4.50 g, 0.019 mol) dissolved in dry THF (20 ml). The mixture was allowed to warm to ambient temperature and stirred overnight. Methanol (1 ml) was added, followed by water and the product extracted using ethyl acetate (3×75 ml). The combined organic layers were washed with water (2×50 ml), dried over anhydrous potassium carbonate and the solvent removed to give the crude product (4.87 g). Column chromatography (flash silica gel; ethyl acetate) gave, after crystallisation from toluene, ethyl 4-(1H-2-methylbenzimidazylmethyl)benzoate (1.61 g, 34%) as a white crystalline solid.

m.p. 80°–82° C.

Analysis calculated for C$_{17}$H$_{16}$N$_2$O$_2$.0.1H$_2$O: Requires C 72.37; H 5.79; N 9.93. Found C 72.40; H 5.81; N 9.95.

i.r. (nujol) 2090, 1810, 1300 cm$^{-1}$ delta$_H$(250 MHz, CDCl$_3$) 8.01 (1H, s), 7.97 (2H, d, J 6.0 Hz), 7.82 (1H, dt, J 6.0 Hz, 1.3 Hz), 7.16–7.37 (5H, m) 5.41 (2H, s), 4.34 (2H, q, J 7.1 Hz), 1.36 (3H, t, J 7.1 Hz).

(c) 4-(1H-2-Methylbenzimidazylmethyl)phenylmethanol

Utilising the procedure described in Example 23(d) employing ethyl 4-(1H-2-methylbenzimidazylmethyl)benzoate in lieu of ethyl 4-(1H-2-methylbenzimidazyl)benzoate gave 4-(1H-2-methylbenzimidazyl)phenylmethanol (93%) as a yellow crystalline solid.

delta$_H$ (250 MHz, CDCl$_3$) 7.71 (1H, m), 7.38–7.19 (6H, m), 7.04 (2H, d, J 8.2 Hz), 5.33 (2H, s), 4.68 (2H, d, J 5.6 Hz), 2.56 (3H, s).

(d)

O-((4-(1H-2-Methylbenzimidiazylmethyl)phenyl)methyl)-5-(3,4-dimethoxyphenyl)-gamma-butyrolactol ether O-((4-(1H-2-Methylbenzimidiazylmethyl)phenyl)methyl)-5-(3,4-dimethoxyphenyl)-gamma-butyrolactol ether was prepared by the procedure described in Example 1(d) employing 4-(1H-2-methylbenzimidazylmethyl)phenylmethanol in lieu of 3-(3-pyridyl)-1-propanol.

1:1 Mixture of trans and cis diastereoisomers: Colourless oil.

delta$_H$(250 MHz, CDCl$_3$) 7.73 (1H, dd, J 6.4, 2.1 Hz), 7.26 (5H, m), 7.02 (2H, dd, J 8.1, 1.9 Hz), 6.85 (3H, m), 5.41 (0.5H, dd, J 5.2, 1.8 Hz, CHOO), 5.28 (2H, s), 5.24 (0.5H, d, J 4.0 Hz, CHOO), 5.00 (1H, m, OCHAr), 4.80 (1H, t, J 12.1 Hz), 4.51 (1H, dd, J 12.1, 3.3 Hz), 3.88, 3.85. 3.37, 3.68, (6H, 4s), 2.56 (3H, 2s), 2.47–1.66 (4H, m).

delta$_C$ (62.90 MHz, CDCl$_3$) 151.77, 148.97, 148.37, 142.25, 138.16, 138.02, 135.46, 135.21, 134.94, 134.59, 128.39, 128.16, 126.20, 122.31, 122.07, 118.91, 118.24, 110.95, 110.71, 109.54, 109.31, 109.01, 103.64, 103.28, 82.96, 79.30, 68.53, 68.16, 63.50, 55.86, 55.79, 55.52, 46.78, 33.90, 32.68, 32.44, 13.78.

EXAMPLE 25

O-(3-(4-(1H-2-Methylbenzimidazyl)phenyl)propyl)-5-(3,4-dimethoxyphenyl)-gamma-butyrolactol ether

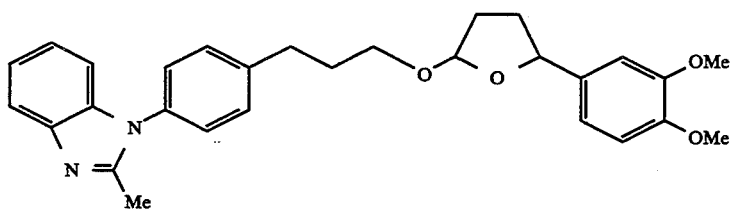

(a) N-(4-Iodophenyl)-2-nitroaniline

A mixture of 2-fluoronitrobenzene (14 g, 100 mmol), 4-iodoaniline (11 g, 50 mmol) and triethylamine (14 ml, 100 mmol) was heated under reflux. After 48 h the reaction mixture was allowed to cool and ethyl acetate (300 ml) was added. The solution was washed with water (2×100 ml), aqueous 2M potassium hydroxide (100 ml) and brine (100 ml). The organics were dried over anhydrous magnesium sulphate and the solvent removed under reduced pressure to give an orange solid. Recrystalisation from ethyl acetate gave N-(4-iodophenyl)-2-nitroaniline (8.2 g, 48%) as an orange crystalline solid. delta$_H$(250 MHz, CDCl$_3$) 9.39 (1H, s), 8.21 (1H, dd, J 8.5, 1.5 Hz), 7.71 (2H, dd, J 8.6, 2.0 Hz), 7.39 (1H, m), 7.24 (1H, m), 7.05 (2H, dd, J 8.6, 1.4 Hz), 6.83 (1H, m).

(b) N-(4-Iodophenyl)-2-aminoaniline

A solution of sodium dithionite (85%, 19.7 g, 96 mmol) in water (100 ml) was added to a suspension of N-(4-iodophenyl)-2-nitroaniline (8 g, 24 mmol) in ethanol (400 ml). The resulting mixture was heated under reflux for 45 min, cooled, treated with dilute aqueous ammonia (300 ml) and concentrated under reduced pressure. The resulting white slurry was treated with dilute aqueous ammonia (200 ml), filtered, the collected solid washed with water (100 ml) and dried to give N-(4-iodophenyl)-2-aminoaniline (3.1 g, 43%) as a white solid.

$delta_H$(250 MHz, CDCl$_3$) 7.48 (2H, d, J 8.0 Hz), 7.09 (2H, m), 6.82 (2H, m), 6.54 (2H, d, J 8.0 Hz), 5.21 (1H, br s), 3.81 (2H, br s).

(c) Iodo-4-(1H-2-methylbenzimidazyl)benzene

Ethyl acetimidate hydrochloride (3.7 g, 30 mmol) was added to a suspension of N-(4-iodophenyl)-2-aminoaniline (3.1 g, 10 mmol) in ethanol (30 ml) at 0° C. The mixture was stirred at room temperature for 2 h, ice cold 2M aqueous potassium hydroxide (50 ml) added and the mixture extracted with ethyl acetate (2×100 ml). The organic layer was washed with water (3×100 ml) dried over anhydrous magnesium sulphate and the solvent removed under reduced pressure to give a white solid. Crystallisation from ethyl acetate gave iodo-4-(1H-2-methylbenzimidazyl)benzene (2.1 g, 62%) as a white crystalline solid.

$delta_H$(250 MHz, CDCl$_3$) 7.91 (2H, dd, J 8.6, 1.9 Hz), 7.74 (1H, dd, J 7.8, 1.0 Hz), 7.31–7.08 (5H, br m), 2.51 (3H, s).

(d) Methyl E-3-(4-(1H-2-methylbenzimidazyl)phenyl)propenoate

Iodo-4-(1H-2-methylbenzimidazyl)benzene (1.6 g, 4.8 mmol), methyl acrylate (0.52 g, 6 mmol), palladium(II) acetate (0.13 g, 0.6 mmol), tri-o-tolylphosphine (0.37 g, 1.2 mmol) and dry acetonitrile (3 ml) were placed in a thick walled glass tube. The tube was sealed under argon and the mixture heated at 90° C. After 12 h the reaction mixture was allowed to cool to room temperature and chloroform (30 ml) was added. The mixture was washed with water (2×50 ml), the organics dried over anhydrous magnesium sulphate, and the solvent removed under reduced pressure. Column chromatography (flash silica gel; ethyl acetate) yielded methyl E-3-(4-(1H-2-methylbenzimidazyl)phenyl)propenoate as an off white solid (1.1 g, 78%).

$delta_H$(250 MHz, CDCl$_3$) 7.90–7.40 (4H, br m), 7.43 (2H, dd, J 8.5, 2.0 Hz), 7.32–7.13 (3H, br m), 6.54 (1H, d, J 16.2 Hz), 3.85 (3H, s), 2.54 (3H, s).

(e) 3-(4-(1H-2-Methylbenzimidazyl)phenyl)-1-propanol

To an ice cold mixture of lithium aluminium hydride (0.19 g, 5.1 mmol) in dry THF (100 ml) was added dropwise a solution of methyl E-3-(4-(1H-2-methylbenzimidazyl)phenyl)propenoate (1 g, 3.4 mmol) in dry THF (50 ml) under argon. The resulting mixture was allowed to warm up to room temperature and stirred for 12 h. Water (0.2 ml), 15% aqueous sodium hydroxide (0.2 ml) and water (0.6 ml) were added sequentially over 0.5 h and the mixture allowed to stir for 1 h. The resulting suspension was filtered and the filtrate concentrated under reduced pressure to give 3-(4-(1H-2-methylbenzimidazyl)phenyl)-1-propanol (0.77 g, 85%) as a yellow solid.

$delta_H$ (250 MHz, CDCl$_3$) 7.75 (1H, d, J 7.7 Hz), 7.70–7.05 (7H, m), 2.84 (2H, t), 2.53 (2H, m), 2.52 (3H, s), 2.05 (2H, m), 1.85 (1H, br s s).

(f) O-(3-(4-(1H-2-Methylbenzimidazyl)phenyl)propyl)-5-(3,4-dimethoxyphenyl)-gamma-butyrolactol ether O-(3-(4-(1H-2-Methylbenzimidazyl)phenyl)propyl)-5-(3,4-dimethoxyphenyl)-gamma-butyrolactol ether was prepared by the procedure described in Example 1(d) employing 3-(4-(1H-2-methylbenzimidazyl)phenyl)-1-propanol as starting material.

20:80 Mixture of trans and cis diastereoisomers: Colourless oil.

$delta_H$ (250 MHz, CDCl$_3$) 7.74 (1H, d, J 7.7 Hz), 7.65–7.10 (7H, m), 6.90–6.70 (3H, m), 5.47 (0.2H, dd, J 5.2, 1.8 Hz, CHOO), 5.36 (0.8H, dd, J 5.3, 1.9 Hz, CHOO), 5.05 (1H, m, OCHAr), 3.91 (0.6H, s), 3.90 (2.4H, s), 3.89 (0.6H, s), 3.87 (2.4H, s), 3.85 (1H, m), 3.55 (1H, dt, J 9.7, 6.4 Hz), 2.83 (2H, t, J 7.3 Hz), 2.52 (0.6H, s), 2.50 (2.4H, s), 2.45–1.70 (6H, m).

EXAMPLE 26

O-((4-(3-Thiazolo[3,2-a]benzimidazyl)phenyl)methyl)-5-(3,4-dimethoxyphenyl)-gamma-butyrolactol ether

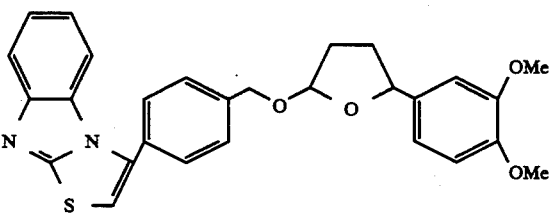

(a) Ethyl 4-(α-(2-benzimidazolylthio)acetophenone)carboxylate

To a stirred suspension of 2-mercaptobenzimidazole (1.50 g, 10 mmol) in ethanol was added 85% potassium hydroxide (0.67 g, 10 mmol). The resulting solution was heated to 80° C. for 30 min and allowed to cool to ambient temperature. Ethyl 4-(bromoacetyl)benzoate (2.71 g, 10 mmol) was added in one portion. A white precipitate formed immediately. The mixture was stirred for 4 h and the precipitate separated by filtration and dried to give ethyl 4-(α-(2-benzimidazolylthio)acetophenone)carboxylate (3.38 g, 100%) as a white solid.

$delta_H$ (250 MHz, CDCl$_3$/DMSO-d6) 7.80 (4H, m), 7.77 (2H, d, J 8.5 Hz), 7.20 (2H, dd, J 6.1, 3.2 Hz), 4.94 (2H, s), 4.02 (2H, q, J 7.1 Hz), 1.04 (3H, t, J 7.1 Hz).

(b) 3-(4-Carboxyethylphenyl)thiazolo[3,2-a]benzimidazole

Titanium tetrachloride (0.5 ml, 4.6 mmol) was added slowly to a stirred solution of ethyl 4-(α-(2-benzimidazolylthio)acetophenone)carboxylate (0.68 g, 2 mmol) under argon at ambient temperature. Evolution of HCl vapour was observed and the solution turned purple. After 5 min the reaction was poured onto ice and DCM added. An insoluble precipitate was removed by filtration and the filtrate partitioned between ethyl acetate and water. The organic phase was separated and washed with a saturated copper sulphate solution, dried over anhydrous sodium sulphate, filtered and concentrated. Column chromatography (flash silica gel; 2% methanol in DCM) gave 3-(4-carboxyethylphenyl)-thiazolo[3,2-a]benzimidazole (0.21 g, 32%) as a white solid.

$delta_H$ (250 MHz, CDCl₃/DMSO-d6) 8.24 (2H, d, J 8.3 Hz), 7.79 (1H, d, J 8.2 Hz), 7.74 (2H, d, J 8.3 Hz), 7.33 (1H, dd, J 8.2, 7.4 Hz), 7.23 (1H, d, J 8.2 Hz), 7.07 (1H, dd, J 8.0, 7.3 Hz), 6.69 (1H, s), 4.46 (2H, q, J 7.1 Hz), 1.46 (3H, t, J 7.1 Hz).

(c)

3-(4-Hydroxymethylphenylthiazolo[3,2-a]benzimidazole

A solution of 3-(4-carboxyethylphenyl)thiazolo[3,2-a]benzimidazole (110 mg, 0.34 mmol) and lithium aluminium hydride (20 mg, 0.53 mmol) in dry THF (5 ml) was stirred at ambient temperature under argon. After 0.5 h water (20 μl), 15% aqueous potassium hydroxide (20 μl) and water (60 μl) were added sequentially. A granular precipitate formed which was removed by washing through a short pad of celite with ethyl acetate. The solvent was removed to give 3-(4-hydroxymethylphenylthiazolo[3,2-a]benzimidazole (57 mg, 61%) as a white amorphous solid.

$delta_H$ (250 MHz, CDCl₃/DMSO-d6) 7.81 (1H, d, J 8.2 Hz), 7.68 (2H, d, J 8.2 Hz), 7.59 (2H, d, J 8.5 Hz), 7.34 (1H, dd, J 8.2, 7.1 Hz), 7.25 (1H, br d), 7.08 (1H, dd, J 8.3, 7.1 Hz), 6.61 (1H, s), 4.88 (2H, s), 1.90 (1H, br s).

(d)

O-((4-(3-Thiazolo[3,2-a]benzimidazyl)phenyl)methyl)-5-(3,4-dimethoxyphenyl)-gamma-butyrolactol ether O-((4-(3-Thiazolo[3,2-a]benzimidazyl)phenyl)methyl)-5-(3,4-dimethoxyphenyl)-gamma-butyrolactol ether was prepared by the procedure described in Example 1(d) employing 3-(4-hydroxymethylphenyl-thiazolo[3,2-a]benzimidazole as starting material.

60:40 Mixture of trans and cis diastereoisomers (21% yield after chromatography): Yellow oil.

$delta_H$ (250 MHz, CDCl₃/DMSO-d6) 7.80 (1H, d, J 8.1 Hz), 7.68–7.55 (4H, m), 7.37–7.25 (2H, m), 7.12–6.83 (4H, m), 6.60 (0.4H, s), 6.59 (0.6H, s), 5.54 (0.6H, dd, J 5.2, 1.9 Hz, CHOO), 5.38 (0.4H, d, J 4.0 Hz, CHOO), 5.17–4.94 (1H, m, OCHAr), 4.70 (0.6H, d, J 3.2 Hz), 4.67 (0.4H, d, J 3.1 Hz), 3.92, 3.90, 3.89, 3.88 (6H, 4s), 2.34–2.13 (4H, m).

EXAMPLE 27

O-((2-(3-Pyridyl)-4-thiazolyl)methyl)-5-(3,4-dimethoxyphenyl)-gamma-butyrolactol ether

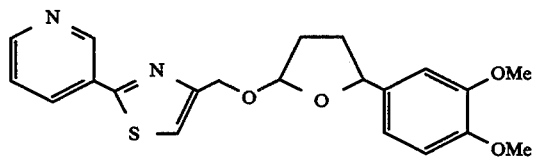

(a) (2-(3-Pyridyl)-4-thiazolyl)methanol

Utilising the procedure described in Example 23(d) employing ethyl 2-(3-pyridyl)-4-thiazolylcarboxylate (commercially available) in lieu of ethyl 4-(1H-benzimidazyl)benzoate gave (2-(3-pyridyl)-4-thiazolyl)methanol (30%) as a yellow crystalline solid.
m.p. 130°–131° C.

$delta_H$ (250 MHz, CDCl₃) 9.17 (1H, d, J 2.1 Hz), 8.66 (1H, dd, J 4.8, 1.5 Hz), 8.23 (1H, dt, J 8.0, 1.9 Hz), 7.39 (1H, dd, J 8.0, 4.8 Hz), 7.28 (1H, d, J 2.9 Hz), 4.87 (2H, s), 2.82 (1H br s).

(b)

O-((2-(3-Pyridyl)-4-thiazolyl)methyl)-5-(3,4-dimethoxyphenyl)-gamma-butyrolactol ether O-((2-(3-Pyridyl)-4-thiazolyl)methyl)-5-(3,4-dimethoxyphenyl)-gamma-butyrolactol ether was prepared by the procedure described in Example 1(d) employing (2-(3-pyridyl)-4-thiazolyl)methanol in lieu of 3-(3-pyridyl)-1-propanol.

60:40 Mixture of trans and cis diastereoisomers (87% yield): Light brown oil.

$delta_H$ (250 MHz, CDCl₃) 9.17 (1H, s), 8.66 (1H, d, J 4.8 Hz), 8.25 (1H, dt, J 6.3, 1.7 Hz), 7.39 (1H, dd, J 7.9, 4.9 Hz), 7.32 (1H, m), 7.05–6.80 (3H, m), 5.55 (0.6H, dd, J 5.1, 1.8 Hz, CHOO), 5.39 (0.4H, d, J 4.0 Hz, CHOO), 5.09 (1H, m, OCHAr), 4.98 (1H, d, J 13.2 Hz), 4.78 (1H, d, J 12.7 Hz), 3.91, 3.88, 3.87, 3.79 (6H, 4s), 2.53–1.71 (4H, m).

$delta_C$ (62.90 MHz, CDCl₃) 164.85, 155.47, 155.33, 150.68, 148.95, 148.38, 147.65, 135.45, 134.52, 133.60, 129.56, 123.60, 118.90, 118.21, 116.57, 116.40, 110.93, 110.73, 109.59, 109.02, 103.97, 103.56, 83.06, 79.42, 64.96, 64.78, 55.86, 55.80, 55.61, 33.96, 32.63, 32.52.

EXAMPLE 28

O-(3-(5-Pyrimidyl)but-3-ynyl)-5-(3,4-dimethoxyphenyl)-gamma-butyrolactol ether

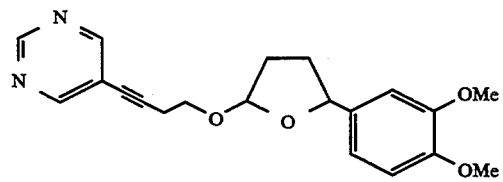

(a) 4-(5-Pyrimidyl)-1-but-3-ynol

Utilising the procedure described in Example 2(a) employing 5-bromopyrimidine in lieu of 3-bromopyridine gave 4-(5-pyrimidyl)-1-but-3-ynol as a colourless oil.

$delta_H$ (250 MHz, CDCl₃) 9.07 (1H, s), 8.72 (2H, s), 4.97 (1H, s), 3.86 (2H, t), 2.72 (2H, t).

(b) O-(3-(5-Pyrimidyl)but-3-ynyl)-5-(3,4-dimethoxyphenyl)-gamma-butyrolactol ether was prepared by the procedure described in Example 1(d) employing 4-(5-pyrimidyl)-1-but-3-ynol as starting material.

Fraction A (trans diastereoisomer) (7% yield after chromatography): Yellow oil.

$delta_H$ (250 MHz, CDCl₃) 9.10 (1H, s), 8.73 (2H, s), 6.85 (3H, m), 5.41 (1H, dd, J 5.3, 1.8 Hz, CHOO), 5.06 (1H, t, J 7.3 Hz, OCHAr), 3.96 (1H, dt, J 9.8, 6.8 Hz), 3.90 (3H, s), 3.88 (3H, s), 3.73 (1H, dt, J 9.7, 6.9 Hz), 2.78 (2H, t, J 6.8 Hz), 2.40 (1H, m), 2.24 (1H, m), 2.04 (1H, m), 1.79 (1H, m).

EXAMPLE 29

O-(3-(3,5-Dimethyl-1,2,4-triazol-4-yl)propyl)-5-(3,4-dimethoxyphenyl)-gamma-butyrolactol ether

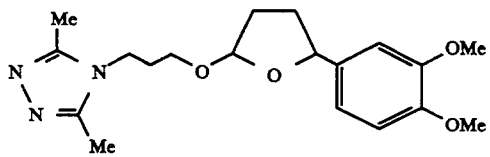

(a) 3-(3,5-Dimethyl-1,2,4-triazol-4-yl)-1-propanol

3-Aminopropanol (0.39 ml, 5.1 mmol), 2,5-dimethyl-1,3,4-oxadiazole (0.50 g, 5.1 mmol) and N-methylpyrrolidone (10 ml) were heated at 150° C. overnight. The solvent was removed under high vacuum. Column chromatography (flash silica gel; 15% methanol in DCM) gave 3-(3,5-dimethyl-1,2,4-triazol-4-4-yl)-1-propanol (75 mg, 9%) as a colourless oil.

delta$_H$(250 MHz, CDCl$_3$) 5.10 (1H, br s), 3.93 (2H, t, J 7.1 Hz), 3.58 (2H, t, J 5.6 Hz), 2.35 (6H, s), 1.84 (2H, quintet).

(b)
O-(3-(3,5-Dimethyl-1,2,4-triazol-4-yl)propyl)-5-(3,4-dimethoxyphenyl)-gamma-butyrolactol ether O-(3-(3,5-Dimethyl-1,2,4-triazol-4-yl)propyl)-5-(3,4-dimethoxyphenyl)-gamma-butyrolactol ether was prepared by the procedure described in Example 1(d) employing 3-(3,5-dimethyl-1,2,4-triazol-4-yl)-1-propanol in lieu of 3-(3-pyridyl)-1-propanol.

1:1 Mixture of trans and cis diastereoisomers (8% yield after chromatography): Brown oil.

delta$_H$ (250 MHz, CDCl$_3$) 6.91–6.81 (3H, m), 5.30 (0.5H, dd, J 5.4, 2.3 Hz, CHOO), 5.15 (0.5H, m, CHOO), 4.99 (1H, t, J 7.3 Hz, OCHAr), 3.90 (3H, s), 3.88 (3H, s), 3.87 (3H, m), 3.43 (1H, m), 2.43 (3H, s), 2.39 (3H, s), 2.38–1.76 (6H, m).

EXAMPLE 30

O-(3-(1H-2-Methylimidazo[4,5-c]pyridyl)propyl)-5-(3,4-dimethoxyphenyl)-gamma-butyrolactol ether

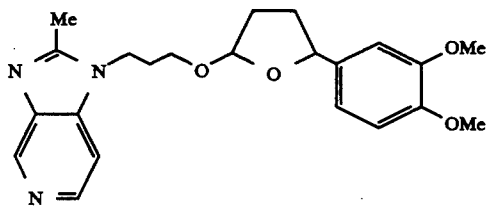

(a) 4-(3-Hydroxypropylamino)-3-nitropyridine

3-Amino-1-propanol (4.5 g, 60.0 mmol) was added slowly to a mixture of 4-chloro-3-nitropyridine (8.0 g, 50.5 mmol) and sodium hydrogen carbonate (4.2 g, 50.0 mmol) in ethanol (200 ml). The mixture was stirred for 3 h at ambient temperature and the solvent removed under reduced pressure. Saturated aqueous sodium hydrogen carbonate (50 ml) was added to the residue, which was extracted with ethyl acetate (3×200 ml). The combined organics were dried over anhydrous sodium sulphate, filtered and evaporated. Crystallisation from ethyl acetate gave 4-(3-hydroxypropylamino)-3-nitropyridine (4.3 g, 43%) as an orange crystalline solid.

delta$_H$(250 MHz, CDCl$_3$) 9.20 (1H, s), 8.48 (1H, br s), 8.28 (1H, d), 6.78 (1H, d), 3.86 (2H, t), 3.53 (2H, q), 2.08 (1H, br s), 2.03 (2H, m).

(b) 3-Amino-4-(3-hydroxypropylamino)pyridine 4-(3-Hydroxypropylamino)-3-nitropyridine (4.12 g, 20.9 mmol) was dissolved in ethanol (130 ml) and Raney nickel (411 mg, 7.0 mmol) added. The stirred mixture was hydrogenated for 3 days. The catalyst was removed by filtration under argon and the solvent removed under reduced pressure to give 3-amino-4-(3-hydroxypropylamino)pyridine as a brown oil which was used directly in the next step.

(c)
1-(3-Acetoxypropyl)-2-methylimidazo[4,5-c]pyridine

Crude 3-amino-4-(3-hydroxypropylamino)pyridine (4.5 g, 27 mmol) was dissolved in acetic anhydride (56 ml) and the mixture heated at reflux overnight. The excess acetic anhydride was removed under reduced pressure and the residue purified by column chromatography (flash silica gel; 5%–50% methanol in DCM) to give 1-(3-acetoxypropyl)-2-methylimidazo[4,5-c]pyridine (1.81 g, 29%) as a colourless oil.

delta$_H$ (250 MHz, CDCl$_3$) 8.98 (1H, s), 8.35 (1H, d), 7.23 (1H, d), 4.23 (2H, t), 4.08 (2H, t), 2.63 (3H, s), 2.13 (2H, m), 2.03 (3H, s).

(d) 3-(1H-2-Methylimidazo[4,5-c]pyridyl)-1-propanol

To a solution of 1-(3-Acetoxypropyl)-2-methylimidazo[4,5-c]pyridine (1.8 g, 7.8 mmol) in ethanol (40 ml), was added slowly aqueous 2M potassium hydroxide (7 ml, 14 mmol) and the resulting mixture stirred for 3 h at room temperature. The solvent was removed under reduced pressure and the residue was treated with 2M hydrochloric acid (50 ml). The solution was washed with DCM (2×100 ml), solid sodium hydrogen carbonate added to pH 7.5, before extraction with DCM (10×100 ml). The combined organics were dried over anhydrous sodium hydrogen carbonate, filtered and evaporated to give 3-(1H-2-methylimidazo[4,5-c]pyridyl)-1-propanol (1.21 g, 82%) as a light brown oil.

delta$_H$ (250 MHz, CDCl$_3$) 8.88 (1H, s), 8.25 (1H, d), 7.33 (1H, d), 4.30 (2H, t), 3.63 (2H, t), 2.63 (3H, s), 2.04 (2H, m).

(e)
O-(3-(1H-2-Methylimidazo[4,5-c]pyridyl)propyl)-5-(3,4-dimethoxyphenyl)-gamma-butyrolactol ether Utilising the procedure described in Example 1(d) employing 3-(1H-2-methylimidazo[4,5-c]pyridyl)-1-propanol (0.50 g, 2.6 mmol) in lieu of 3-(3-pyridyl)-1-propanol gave O-(3-(1H-2-methylimidazo[4,5-c]pyridyl)propyl)-5-(3,4-dimethoxyphenyl)-gamma-butyrolactol ether (0.16 g, 15%).

65:35 Mixture of trans and cis diastereoisomers: Pale yellow oil.

delta$_H$(250 MHz, CDCl$_3$) 8.93 (1H, br s), 8.31 (1H, br d, J 4.4 Hz), 7.22 (1H, m), 6.90–6.75 (3H, m), 5.22 (0.65H, dd, J 4.7, 2.5 Hz, CHOO), 5.06 (0.35H, d, J 1.9 Hz, CHOO), 4.91 (1H, m, OCHAr), 4.20 (1.3H, t, J 7.0 Hz), 4.14 (0.7H, t, J 6.6 Hz), 3.83, 3.81, 3.80, 3.79 (6H, 4s), 3.75 (1H, m), 3.35 (1H, m), 2.60 (1.95H, s), 2.55 (1.05H, s), 2.40–1.64 (6H, m).

The trans and cis diastereoisomers were separated by preparative high performance liquid chromatography ($C_{18}$ reverse phase column; 40:60 methanol/aqueous 0.01M ammonium phosphate).

Fraction A (cis diastereoisomer) : Colourless oil.

$delta_H$ (250 MHz, $CDCl_3$) 8.98 (1H, br s), 8.37 (1H, br s), 7.26 (1H, d, J 6.8 Hz), 6.95–6.78 (3H, m), 5.12 (1H, t, J 2.3 Hz, CHOO), 4.98 (1H, t, J 7.7 Hz, OCHAr), 4.17 (2H, t, J 6.7 Hz), 3.86 (3H, s), 3.84 (3H, s), 3.81 (1H, m), 3.36 (1H, dt, J 10.3, 6.2 Hz), 2.62 (3H, s), 2.28 (1H, m), 2.15–1.92 (5H, m).

Fraction B (trans diastereoisomer): Colourless oil.

$delta_H$ (250 MHz, $CDCl_3$) 8.97 (1H, s), 8.36 (1H, d, J 5.6 Hz), 7.29 (1H, d, J 5.7 Hz), 6.83 (3H, m), 5.25 (1H, dd, J 5.2, 2.2 Hz, CHOO), 4.95 (2H, t, J 7.1 Hz, OCHAr), 4.25 (2H, dt, J 6.9, 1.4 Hz), 3.87 (3H, s), 3.85 (3H, s), 3.78 (1H, dt, J 10.8, 6.0 Hz), 3.38 (1H, dt, J 10.4, 6.7 Hz), 2.65 (3H, s), 2.35 (1H, m), 2.21 (1H, m), 2.08 (2H, m), 1.96 (1H, m), 1.76 (1H, m).

EXAMPLE 31

O-(4-(1H-2-Methylimidazo[4,5-c]pyridyl)butyl)-5-(3,4-dimethoxyphenyl)-gamma-butyrolactol ether

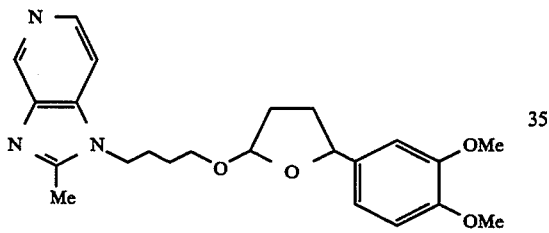

O-(4-(1H-2-Methylimidazo[4,5-c]pyridyl)butyl)-5-(3,4-dimethoxyphenyl)-gamma-butyrolactol ether was prepared by the procedures described in Example 30(a)–(e) employing 4-amino-1-butanol in lieu of 3-amino-1-propanol in the initial step (Example 30 (a)).

65:35 Mixture of trans and cis diastereoisomers: Pale yellow oil.

$delta_H$ (250 MHz, $CDCl_3$) 8.95 (1H, br s), 8.35 (1H, br d), 7.21 (1H, m), 6.90–6.71 (3H, m), 5.28 (0.65H, dd, J 5.2, 2.0 Hz, CHOO), 5.12 (0.35H, d, J 1.9 Hz, CHOO), 4.94 (1H, m, OCHAr), 4.13 (1.3H, t, J 7.4 Hz), 4.09 (0.7H, t, J 7.4 Hz), 3.85, 3.83, 3.81, 3.79 (6H, 4s), 3.80 (1H, m), 3.43 (1H, m), 2.61 (1.95H, s), 2.58 (1.05H, s), 2.40–1.55 (8H, m).

EXAMPLES 32–37

The compounds of Examples 32–37 were prepared by the method of Example 15(b) starting from 3-(1H-2-methylimidazo[4,5-c]pyridyl)-1-propanol and the appropriate lactol. For the preparation of Examples 33, 35 and 37 a catalytic amount of 4-N,N-dimethylaminopyridine was utilised in the coupling step and for Examples 35 and 37 the reaction was conaucted at reflux.

32.

O-(3-(1H-2-Methylimidazo[4,5-c]pyrid-1-yl)propyl)-5-phenyl-gamma-butyrolactol ether

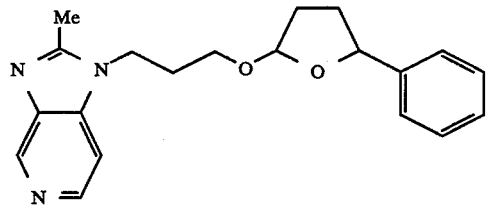

1:1 Mixture of trans and cis diastereoisomers (34% yield after chromatography): Yellow oil.

$delta_H$ (250 MHz, $CDCl_3$) 8.97 (1H, br s), 8.34 (1H, br s), 7.40–7.20 (6H, m), 5.27 (0.5H, dd, J 5.3, 2.1 Hz, CHOO), 5.13 (0.5H, t, J 2.4 Hz, CHOO), 5.02 (1H, t, J 7.2 Hz, OCHAr), 4.21 (2H, m), 3.80 (1H, m), 3.37 (1H, m), 2.64 (1.5H, s), 2.59 (1.5H, s), 2.45–1.70 (6H, m).

$delta_C$ (62.90 MHz, $CDCl_3$) 153.32, 142.80, 141.89, 141.63, 141.46, 140.07, 128.33, 128.26, 127.46, 127.40, 126.05, 125.65, 104.69, 104.23, 82.45, 79.66, 63.82, 63.32, 41.03, 40.93, 33.73, 32.83, 32.46, 32.29, 29.64, 29.55.

33.

O-(3-(1H-2-Methylimidazo[4,5-c]pyridyl)propyl)-5-(4-fluorophenyl)-gamma-butyrolactol ether

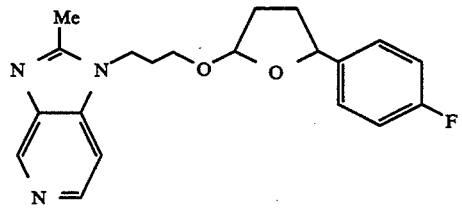

1:1 Mixture of trans and cis diastereoisomers (13% yield after chromatography): Yellow oil.

$delta_H$ (250 MHz, $CDCl_3$) 8.85 (1H, s), 8.21 (1H, d, J 5.6 Hz), 7.15 (3H, m), 6.86 (2H, m), 5.12 (0.5H, dd, J 5.3, 2.0 Hz, CHOO), 4.97 (0.5H, dd, J 3.2, 2.1 Hz, CHOO), 4.86 (1H, t, J 7.0 Hz, OCHAr), 4.07 (2H, m), 3.63 (1H, m), 3.22 (1H, m), 2.50 (1.5H, s), 2.46 (1.5H, s), 2.35–1.50 (6H, m).

$delta_C$ (62.90 MHz, $CDCl_3$) 161.82 (d, J 233.4 Hz), 153.13, 153.07, 141.19, 141.10, 139.79, 139.73, 139.51, 138.44, 137.59, 127.46 (d, J 7.6 Hz), 127.09 (d, J 8.2 Hz), 114.79 (d, J 22.0 Hz), 114.75 (d, J 22.0 Hz), 104.58, 104.52, 104.34, 103.85, 81.52, 78.66, 63.56, 63.06, 40.69, 40.57, 33.39, 32.64, 32.16, 32.12, 29.26, 29.14, 12.26.

34.

O-(3-(1H-2-Methylimidazo[4,5-c]pyridyl)propyl)-5-(4-bromophenyl)-gamma-butyrolactol ether

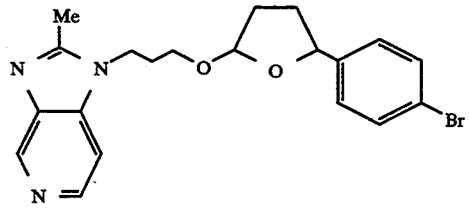

1:1 Mixture of trans and cis diastereoisomers (7% yield after chromatography): Yellow oil.

delta$_H$ (250 MHz, CDCl$_3$) 8.95 (1H, s), 8.34 (1H, d, J 5.5 Hz), 7.43 (2H, dd, J 8.6, 2.4 Hz), 7.33–7.11 (3H, m), 5.24 (0.5H, dd, J 5.3, 2.0 Hz, CHOO), 5.10 (0.5H, t, J 2.7 Hz, CHOO), 4.96 (1H, m, OCHAr), 4.21 (2H, m), 3.76 (1H, m), 3.37 (1H, m), 2.64 (1.5H, s), 2.60 (1.5H, s), 2.45–1.65 (6H, m).

delta$_C$ (62.90 MHz, CDCl$_3$) 153.45, 141.98, 141.28, 141.14, 140.31, 139.70, 131.38, 127.77, 127.36, 121.16, 104.86, 104.70, 104.32, 81.73, 78.97, 63.88, 63.40, 41.09, 40.96, 33.64, 32.85, 32.32, 29.59, 29.47, 13.70.

35.
O-(3-(1H-2-Methylimidazo[4,5-c]pyridyl)propyl)-5-(3,4-dichlorophenyl)-gamma-butyrolactol ether

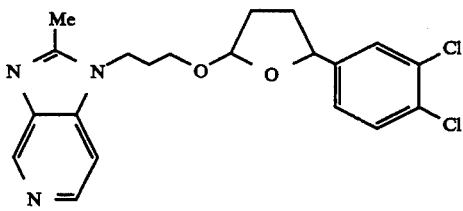

1:1 Mixture of trans and cis diastereoisomers (24% yield after chromatography): Yellow oil.

delta$_H$ (250 MHz, CDCl$_3$) 8.93 (1H, s), 8.31 (1H, d, J 5.5 Hz), 7.43–7.19 (3H, m), 7.06 (1H, m), 5.22 (0.5H, dd, J 5.2, 3.5 Hz, CHOO), 5.06 (0.5H, br s, CHOO), 4.91 (1H, m, OCHAr), 4.25–4.10 (2H, m), 3.74 (1H, m), 3.33 (1H, m), 2.59 (1.5H, s), 2.57 (1.5H, s), 2.40–1.60 (6H, m).

36.
O-(3-(1H-2-Methylimidazo[4,5-c]pyridyl)propyl)-5-(3-chloro-4-methoxyphenyl)-gamma-butyrolactol ether

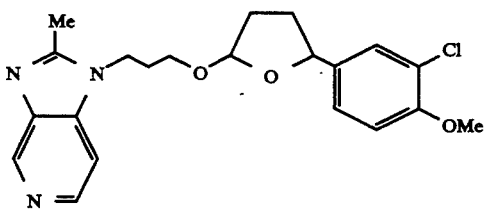

1:1 Mixture of trans and cis diastereoisomers (31% yield after chromatography): Yellow oil.

delta$_H$ (250 MHz, CDCl$_3$) 8.91 (1H, s), 8.28 (1H, d, J 5.6 Hz), 7.34 (0.5H, d, J 2.1 Hz), 7.26 (0.5H, d, 2.1 Hz), 7.21 (0.5H, dd, J 5.7, 0.8 Hz), 7.19 (0.5H, dd, J 5.4, 0.8 Hz), 7.08 (1H, dd, J 8.4, 2.0 Hz), 6.80 (1H, t, J 8.4 Hz), 5.18 (0.5H, dd, J 5.3, 2.1 Hz, CHOO), 5.03 (0.5H, t, J 1.9 Hz, CHOO), 4.85 (1H, m, OCHAr), 4.18 (2H, m), 3.80 (3H, 2s), 3.72 (1H, m), 3.30 (1H, m), 2.58 (1.5H, s), 2.55 (1.5H, s), 2.35–1.55 (6H, m).

delta$_C$ (62.90 MHz, CDCl$_3$) 154.08, 153.20, 141.43, 141.32, 139.95, 139.87, 139.68, 136.10, 135.04, 128.03, 127.48, 125.55, 125.06, 122.20, 111.74, 111.56, 104.66, 104.46, 104.05, 81.42, 78.54, 63.73, 63.29, 55.98, 40.86, 33.53, 32.67, 32.25, 29.45, 29.37, 13.60.

37.
O-(3-(1H-2-Methylimidazo[4,5-c]pyridyl)propyl)-5-(3,4,5-trimethoxyphenyl)-gamma-butyrolactol ether

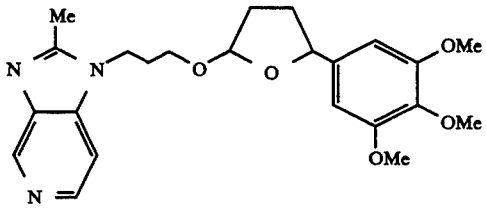

1:1 Mixture of trans and cis diastereoisomers (21% yield after chromatography): Pale yellow oil.

delta$_H$ (250 MHz, CDCl$_3$) 8.95 (1H, s), 8.33 (1H, m), 7.27 (0.5H, dd, J 5.4, 1.5 Hz), 7.23 (0.5H, d, J 5.7 Hz), 6.58 (1H, m), 6.50 (1H, s), 5.25 (0.5H, dd, J 5.3, 2.0 Hz, CHOO), 5.09 (0.5H, d, J 2.5 Hz, CHOO), 4.91 (1H, m, OCHAr), 4.27–4.17 (2H, m), 3.84 (3H, s), 3.80 (6H, 2 s), 3.79 (1H, m), 3.36 (1H, m), 2.64 (1.5H, s), 2.60 (1.5H, s), 2.40–1.65 (6H, m).

COMPARATIVE EXAMPLE

O-(3-(3-N-methylpyridyl)propyl)-5-(3,4-dimethoxyphenyl)-gamma-butyrolactol ether iodide This compound is not within the scope of the invention: It has been included here as a comparative example. A series of 5-oxy derivatives of tetrahydofuran which possess a quaternised nitrogen heterocycle are described in U.S. Pat. No. 4,888,337. The comparative example, whilst not described in U.S. Pat. No. 4,888,337, provides the most direct comparison between the teaching of U.S. Pat. No. 4,888,337 and that of the invention.

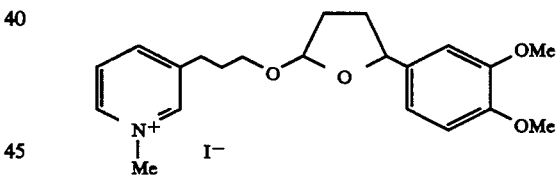

(A) Trans diastereoisomer

A solution of trans-O-(3-(3-pyridyl)propyl)-5-(3,4-dimethoxyphenyl)-gamma-butyrolactol ether (Example 1A) (102 mg, 0.30 mmol), methyl iodide (0.1 ml, 1.6 mmol) in DCM (10 ml) was stirred at room temperature overnight. The solvent and excess methyl iodide was removed under reduced pressure. The residue was taken up in ethyl acetate and filtered through a pad of flash silica gel. Elution with ethyl acetate removed unreacted trans-O-(3-(3-pyridyl)propyl)-5-(3,4-dimethoxyphenyl)-gamma-butyrolactol ether. Elution with methanol, concentration, dissolution in DCM, filtration and concentration gave trans-O-(3-(3-N-methylpyridyl)propyl)-5-(3,4-dimethoxyphenyl)-gamma-butyrolactol ether iodide (103 mg, 71%) as a yellow oil.

delta$_H$ (250 MHz, CDCl$_3$) 9.01 (1H, d, J 6.3 Hz), 8.97 (1H, s), 8.27 (1H, d, J 8.1 Hz), 8.00 (1H, dd, J 7.9, 6.1 Hz), 6.85 (3H, m), 5.32 (1H, dd, J 5.2, 2.1 Hz, CHOO), 5.01 (1H, t, J 7.1 Hz, OCHAr), 4.52 (3H, s), 3.87 (3H, s), 3.84 (3H, s), 3.72 (1H, m), 3.51 (1H, m), 2.98 (2H, t, J 7.6

Hz), 2.36 (1H, m), 2.20 (1H, m), 2.10–1.85 (3H, m), 1.73 (1H, m).

(B) Cis diastereoisomer

Following the above procedure utilising cis-O-(3-(3-pyridyl)propyl)-5-(3,4-dimethoxyphenyl)-gamma-butyrolactol ether (Example 1B) (147 mg, 0.43 mmol) as starting material gave cis-O-(3-(3-N-methylpyridyl)-propyl)-5-(3,4-dimethoxyphenyl)-gamma-butyrolactol ether iodide (162 mg, 78%) as a yellow oil.

delta$_H$ (250 MHz, CDCl$_3$) 9.04 (1H, d, J 6.0 Hz), 9.02 (1H, s), 8.17 (1H, d, J 8.1 Hz), 7.93 (1H, dd, J 8.0, 6.0 Hz), 6.91 (3H, m), 5.16 (1H, t, J 2.5 Hz, CHOO), 4.94 (1H, m, OCHAr), 4.55 (3H, s), 3.86 (3H, s), 3.85 (3H, s), 3.79 (1H, dt, J 10.3, 6.0 Hz), 3.50 (1H, dt, J 10.4, 6.1 Hz), 2.95 (2H, t, J 7.6 Hz), 2.26 (1H, m), 2.12–1.93 (5H, m).

Note on the Assignment of Relative Stereochemistry

The compounds of the invention include both the trans and the cis diastereoisomers about the gamma-butyrolactol ring. The assignment of the relative stereochemistry of the examples described above is by analogy with trans and cis-O-(2-(3-pyridyl)ethyl)-5-(3,4-dimethoxyphenyl)-gamma-butyrolactol ether, a compound which is not within the scope of the invention. Differential NOE NMR experiments were used to determine the relative stereochemistry of trans and cis-O-(2-(3-pyridyl)ethyl)-5-(3,4-dimethoxyphenyl)-gamma-butyrolactol ether, which was prepared by the procedure described in Example 1(d) employing 2-(3-pyridyl)-1-ethanol as starting material. The diastereoisomers were separated by column chromatography (flash silica gel; 5% methanol in ethyl acetate) to give the trans diastereoisomer (fraction A) followed by the cis diastereoisomer (fraction B).

Trans-O-(2-(3-pyridyl)ethyl)-5-(3,4-dimethoxyphenyl)-gamma-butyrolactol ether (Fraction A): Yellow oil.

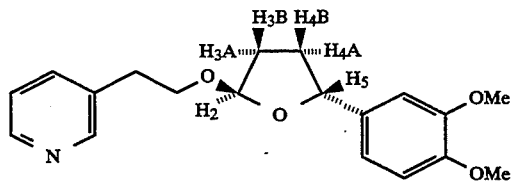

delta$_H$ (250 MHz, CDCl$_3$) 8.49 (1H, s, Py H-2), 8.44 (1H, d, J 4.1 Hz, Py H-6), 7.54 (1H, dt, J 7.8, 1.8 Hz, Py H-4), 7.19 (1H, dd, J 7.7, 4.8 Hz, Py H-5), 6.81 (3H, br s, aryl-H), 5.29 (1H, dd, J 5.2, 1.8 Hz, H-2), 4.84 (1H, t, J 7.2 Hz, H-5), 3.97 (1H, dt, J 9.7, 6.7 Hz, CHHO), 3.86 (3H, s, OCH$_3$), 3.83 (3H, s, OCH$_3$), 3.66 (1$\overline{\text{H}}$, dt, J 9.7, 6.5 Hz, CHHO), 2.88 (2H, t, J 6.6 Hz, PyCH$_2$CH$_2$O), 2.29 (1H, m, H-4B), 2.15 (1H, m, H-3A), 1.9$\overline{2}$ (1H, m, H-3B), 1.68 (1H, m, H-4A). The coupling of H-2 to H-3A and H-3B and of H-5 to H-4A and H-4B was confirmed by a COSY 2D NMR experiment. In differential NOE NMR experiments conducted at 500 MHz; irradiation of H-4B showed enhancements to H-5 (7.5%), H-3B (6%), and H-4A (24%); irradiation of H-3A showed enhancements to H-2 (8%), H-3B (21%) and H-4A (5%); irradiation of H-3B showed enhancements to H-2 (5%), H-5 (3%), H-3A (22%) and H-4B (5%); irradiation of H-4A showed enhancements to H-4B (24%) and H-3A (5%); irradiation of H-2 showed enhancements to H-3A (9%), H-3B (3%) but no enhancement to H-5 was observed; irradiation of H-5 showed an enhancement to H-4B (7%) but no enhancement of H-2 was observed.

delta$_C$ (62.90 MHz, CDCl$_3$) 150.23, 148.82, 148.22, 147.42, 136.20, 134.61, 134.51, 123.01, 118.10, 110.82, 108.88, 104.06, 79.04, 67.18, 55.75, 55.66, 33.34, 32.52, 32.34.

Cis-O-(2-(3-pyridyl)ethyl)-5-(3,4-dimethoxyphenyl)-gamma-butyrolactol ether (Fraction B): Yellow oil.

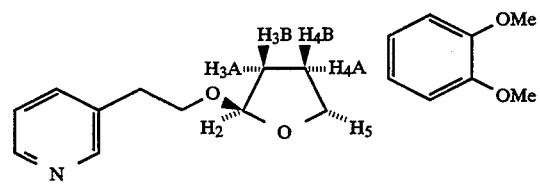

delta$_H$ (250 MHz, CDCl$_3$) 8.50 (1H, s, Py H-2), 8.47 (1H, dd, J 4.7, 0.8 Hz, Py H-6), 7.54 (1H, dt, J 7.8, 1.7 Hz, Py H-4), 7.20 (1H, dd, J 7.8, 4.9 Hz, Py H-5), 6.95–6.74 (3H, m, aryl-H), 5.17 (1H, d, J 3.8 Hz, H-2), 4.95 (1H, m, H-5), 4.03 (1H, dt, J 9.7, 6.8 Hz, CHHO), 3.87 (3H, s, OCH$_3$), 3.84 (3H, s, OCH$_3$), 3.66 (1$\overline{\text{H}}$, dt, J 9.7, 6.8 Hz, CHHO), 2.91 (2H, t, J 6.7 Hz, PyCH$_2$C-H$_2$O), 2.30–1.90 ($\overline{\text{4H}}$, m, H-3A&B, H-4A&B). In differential NOE NMR experiments conducted at 500 MHz irradiation of H-2 showed an enhancement to H-5 (1%) and irradiation of H-5 showed an enhancement to H-2 (1%).

delta$_C$ (62.90 MHz, CDCl$_3$) 150.37, 148.83, 148.33, 147.67, 136.37, 135.44, 134.57, 123.16, 118.63, 110.90, 104.13, 82.75, 67.41, 55.89, 55.70, 33.86, 33.45, 32.67.

PHARMACOLOGY EXAMPLE 1

The inhibition of [$^3$H]-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5mM MgCl$_2$, 2 mM EDTA, pH 7.0), snap freezed in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained [$^3$H]-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM $MgCl_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

% Inhibition = [(TB−TBA)/SB]×100 where the specific binding SB=TB−NSB

Table 1 lists results from this assay for inhibition of [$^3$H]-PAF receptor binding for illustrative examples of the compounds of this invention.

TABLE 1

Results for inhibition of [$^3$H]-PAF receptor binding

| Example | Inhibition of [$^3$H]-PAF binding $IC_{50}$ μM |
|---|---|
| 1A | 4 |
| 1B | 0.15 |
| 2 | 4 |
| 3 | 6 |
| 4 | 5 |
| 5A | 12 |
| 5B | 1.5 |
| 6A | 3 |
| 7A | 12 |
| 7B | 2 |
| 10A | 1 |
| 10B | 0.15 |
| 12 | 3 |
| 23 | 0.9 |
| 24 | 2 |
| 27 | 10 |
| 29 | 0.25 |
| 30 | 0.015 |
| 30A | 0.025 |
| 30B | 0.007 |
| 33 | 0.007 |
| 34 | 0.01 |
| 35 | 0.005 |
| 36 | 0.003 |
| Comparative Example A | 3 |

TABLE 1-continued

Results for inhibition of [$^3$H]-PAF receptor binding

| Example | Inhibition of [$^3$H]-PAF binding $IC_{50}$ μM |
|---|---|
| Comparative Example B | 1 |

PHARMACOLOGY EXAMPLE 2

The activity of the compounds of general formula I is also demonstrated in vivo by their ability to reverse the hypotension caused by an infusion of PAF in rats. Male Sprague-Dawley rats (300–400 g) were anaesthetised with a mixture of sodium pentobarbitone, 22.5 mg·kg$^{-1}$ and thiopental 62.5 mg·kg$^{-1}$. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng·kg$^{-1}$·min$^{-1}$ was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response ($ED_{50}$) calculated by straight line interpolation and the results are presented in Table 2.

TABLE 2

Results for inhibition of PAF-induced hypotension in the rat

| Example | $ED_{50}$ (μg/kg i.v.) |
|---|---|
| 1A | 27 |
| 1B | 9 |
| 27 | 120 |
| 30 | 1 |
| 31 | 3 |
| 33 | 1 |
| 35 | 2 |
| 36 | 2 |
| Comparative Example A | >1000 (31% inhibition @ 1 mg/kg) |
| Comparative Example B | >1000 (10% inhibition @ 1 mg/kg) |

PHARMACOLOGY EXAMPLE 3

The inhibition of PAF induced bronchoconstriction was measured in anaesthetised artificially ventilated guinea-pigs (450–500 g) using a modified version of the Konzett-Rössler technique (Konzett M and Rössler R, *Naunym-Schmiedeb. Arch. Exp. Pathol. Pharmakol.*, 1940, 197, 71). Male Dunkin-Hartley guinea-pigs were anaesthetised with urethane, 1.6 g·kg$^{-1}$. Through a midline neck incision, the trachea was cannulated and the animal ventilated with a constant tidal volume set between 5 and 15 ml, to give a tracheal inflation pressure of 15 mmHg at a rate of 40 per minute. A carotid artery was cannulated for the measurement of blood pressure and heart rate and both jugular veins were cannulated, one for the infusion of PAF and the other for the administration of test compounds. PAF, 40 ng·kg$^{-1}$·min$^{-1}$, was infused i.v. to produced a 100% increase in tracheal inflation pressure, and bronchoconstrictor effects were determined. The dose of test compound which resulted in a 50% reversal of the PAF-induced bronchoconstriction (ED$_{50}$) was calculated and the results are presented in Table 3.

TABLE 3

Results for inhibition of PAF-induced Bronchoconstriction in the guinea pig

| Example | ED$_{50}$ (µg/kg i.v.) |
|---|---|
| 1B | 2.1 |
| 30 | 0.4 |

PHARMACOLOGY EXAMPLE 4

Rats were anaesthetised with a mixture of sodium pentobarbitone, 22.5 mg·kg$^{-1}$, and thiopental, 62.5 mg·kg$^{-1}$. The animals breathed spontaneously, air enriched with oxygen, and a carotid artery was cannulated for the measurement of blood pressure and heart rate. *E. coli* acetone powder serotype No. 0111:B4 (endotoxin) 100 mg·kg$^{-1}$, was administered via a jugular vein; this resulted in a hypotension of approximately 50 mmHg which was sustained for up to 2 hours. Test compounds were administered i.v. via the other jugular vein as a bolus.

The dose which resulted in a 50% reversal of the endotoxin induced hypotension (ED$_{50}$) was calculated by straight line interpolation between the mean responses, calculated from bracketing doses, giving one dose per compound per animal. The results are presented in Table 4.

TABLE 4

Results for inhibition of endotoxin induced hypotension in the rat

| Example | ED$_{50}$ (µg/kg i.v.) |
|---|---|
| 1B | 18 |
| 30B | 7 |

We claim:

1. A compound of general formula I:

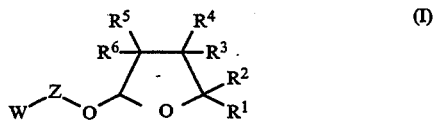

wherein:

W represents an imidazo[4,5-c]pyridyl group, optionally substituted with one or more substituents selected from C$_1$-C$_6$ alkyl, C$_1$-C$_6$ alkoxy, halo, CF, and CN;

Z represents a divalent alkanediyl group from 2 to 8 carbon atoms which may be a straight or branched-chain having at least 3 carbon atoms in the chain linking W to the oxygen atom;

R$^1$ represents a V group wherein V is a

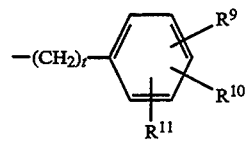

group wherein t is zero and each of R$^9$, R$^{10}$ and R$^{11}$ is independently hydrogen, C$_1$-C$_6$ alkyl, C$_1$-C$_6$ alkoxy, C$_1$-C$_6$ alkylthio, halo, CN, NO$_2$, SOC$_1$-C$_6$ alkyl, SO$_2$C$_1$-C$_6$ alkyl, SO$_2$(CH$_2$)$_{1-4}$CH$_2$OH, SO$_2$NH$_2$, CO$_2$H, CO$_2$C$_1$-C$_6$ alkyl, CHO, COC$_1$-C$_6$ alkyl, CH$_2$OH, OH, benzyl, benzoyl, CF$_3$, CONH$_2$, NHCOC$_1$-C$_6$ alkyl, or an NR$^{15}$R$^{16}$ group wherein each of R$^{15}$ and R$^{16}$ is independently hydrogen or C$_1$-C$_6$ alkyl; and each of R$^2$, R$^3$, R$^4$, R$^5$, and R$^6$ represents hydrogen; or a pharmaceutically or veterinarily acceptable acid addition salt or hydrate thereof.

2. A compound according to claim 1 wherein W represents a 1H-2-methylimidazo[4,5-c]pyridyl group.

3. A compound according to claim 1 wherein the grouping W—Z—O— and the substituent R$^1$ are in the cis configuration with respect to the lactone ring.

4. A compound according to claim 1 wherein the grouping W—Z—O— and the substituent R$^1$ are in the trans configuration with respect to the lactone ring.

5. A compound according to claim 1 which is O-(3-(1H-2-methylimidazo[4,5-c]pyridyl)propyl)-5-(3,4-dimethoxyphenyl)-gamma-butyrolactol ether.

6. A compound according to claim 1 which is O-(4-(1H-2-methylimidazo[4,5c]pyridyl)butyl)-5-(3,4-dimethoxyphenyl)-gamma-butyrolactol butyrolactol ether.

7. A compound according to claim 1 which is O-(3-(1H-2-methylimidazo[4,5-c]pyridyl)propyl)-5-gamma-butyrolactol ether.

8. A compound according to claim 1 which is O-(3-(1H-2-methylimidazo[4,5-c]pyridyl)propyl)-5-(4-fluorophenyl)-gamma-butyrolactol ether.

9. A compound according to claim 1 which is O-(3-(1H-2-methylimidazo[4,5-c]pyridyl)propyl)-5-(4-bromophenyl)-gamma-butyrolactol ether.

10. A compound according to claim 1 which is O-(3-(1H-2-methylimidazo[4,5-c]pyridyl)propyl)-5-(3,4-dichlorophenyl)-gamma-butyrolactol ether.

11. A compound according to claim 1 which is O-(3-(1H-2-methylimidazo[4,5-c]pyridyl)propyl)-5-(3-chloro-4-methoxyphenyl)-gamma-butyrolactol ether.

12. A compound according to claim 1 which is O-(3-(1H-2-methylimidazo[4,5-c]pyridyl)propyl)-5-(3,4,5-trimethoxyphenyl)-gamma-butyrolactol ether.

* * * * *